(12) United States Patent
Dutta et al.

(10) Patent No.: US 12,121,588 B2
(45) Date of Patent: Oct. 22, 2024

(54) LARGE SCALE PRODUCTION PROCESS FOR CAPPED AND UN-CAPPED ANTIBODY CYSTEINES AND THEIR USE IN THERAPEUTIC PROTEIN CONJUGATION

(71) Applicant: PFIZER INC., New York, NY (US)

(72) Inventors: Kaushik Dutta, River Edge, NJ (US); Jose Manuel Gomes, Kingston, NH (US); Frank W. Kotch, Pearl River, NY (US); Vimalkumar B. Patel, Jersey City, NJ (US); Amarnauth Shastrie Prashad, New City, NY (US); Renee L. Procopio-Melino, Andover, MA (US); Xiaotian Zhong, Wayland, MA (US)

(73) Assignee: PFIZER INC., New York, NY (US)

( * ) Notice: Subject to any disclaimer, the term of this patent is extended or adjusted under 35 U.S.C. 154(b) by 1132 days.

(21) Appl. No.: 16/480,792

(22) PCT Filed: Feb. 1, 2018

(86) PCT No.: PCT/IB2018/050638
§ 371 (c)(1),
(2) Date: Jul. 25, 2019

(87) PCT Pub. No.: WO2018/146585
PCT Pub. Date: Aug. 16, 2018

(65) Prior Publication Data
US 2019/0381182 A1 Dec. 19, 2019

Related U.S. Application Data

(60) Provisional application No. 62/618,169, filed on Jan. 17, 2018, provisional application No. 62/532,262, filed on Jul. 13, 2017, provisional application No. 62/456,293, filed on Feb. 8, 2017.

(51) Int. Cl.
| | |
|---|---|
| A61K 47/42 | (2017.01) |
| A61K 47/50 | (2017.01) |
| A61K 47/64 | (2017.01) |
| A61K 47/68 | (2017.01) |
| C07B 31/00 | (2006.01) |
| C07B 33/00 | (2006.01) |
| C07K 1/00 | (2006.01) |
| C07K 16/30 | (2006.01) |
| C07K 1/107 | (2006.01) |
| C07K 1/20 | (2006.01) |

(52) U.S. Cl.
CPC ...... *A61K 47/6843* (2017.08); *A61K 47/6855* (2017.08); *A61K 47/6889* (2017.08); *C07K 1/00* (2013.01); *C07K 16/3015* (2013.01); *C07K 1/1077* (2013.01); *C07K 1/20* (2013.01); *C07K 2317/14* (2013.01)

(58) Field of Classification Search
None
See application file for complete search history.

(56) References Cited

U.S. PATENT DOCUMENTS

| | | | |
|---|---|---|---|
| 8,232,075 | B2 | 7/2012 | Luan et al. |
| 2008/0108553 | A1 | 5/2008 | Luan et al. |
| 2008/0306246 | A1 | 12/2008 | Heywood |
| 2008/0311134 | A1 | 12/2008 | Junutula |
| 2013/0330350 | A1 | 12/2013 | Dimasi |
| 2016/0347824 | A1 | 12/2016 | Meyer |

FOREIGN PATENT DOCUMENTS

| | | |
|---|---|---|
| CA | 3052539 | 8/2018 |
| CN | 1355842 | 6/2002 |
| CN | 104152395 | 11/2014 |
| JP | 2002534119 | 10/2002 |
| WO | 0042175 | 7/2000 |
| WO | WO2009099728 | 8/2009 |
| WO | 2012064733 A2 | 5/2012 |
| WO | 2015123265 A1 | 8/2015 |
| WO | 2015140708 A1 | 9/2015 |
| WO | 2015157595 A1 | 10/2015 |
| WO | 2015162563 | 10/2015 |
| WO | 2016014360 A1 | 1/2016 |
| WO | 2017025897 A2 | 2/2017 |

(Continued)

OTHER PUBLICATIONS

Agarwal et al., Bioconjugate Chem. 26:176-192 (2015) (Year: 2015).*
Junutula et al., Nat. Biotechn. 26:925-932 (2008) (Year: 2008).*
BD Editors, Biology Dictionary, available online at https://biologydictionary.net/oxidizing-agent/, 3 pages (2019) (Year: 2019).*
Kerafast, "Protein Cysteine Oxidation," available online at www.kerafast.com/cat/113/protein-cysteine-oxidation, 12 pages (accessed on Feb. 22, 2023) (Year: 2023).*
ChemTalk, "Common Oxidizing Agents and Reducing Agents," available online at https://chemistrytalk.org/oxidizing-reducing-agents/, 6 pages (accessed on Feb. 22, 2023) (Year: 2023).*
Hull, E.A.: "Antibody Conjugates via Disulfide Bridging", Ph.D. Thesis, University College London, 2014, p. 211; abstract, pp. 31-56.

(Continued)

*Primary Examiner* — Thea D'Ambrosio
(74) *Attorney, Agent, or Firm* — Saul Ewing LLP; Kathryn Doyle; Domingos J. Silva

(57) ABSTRACT

Optimizing production of selectively capped, and uncapped, cysteines on antibodies by manipulation of cell growth conditions including the deliberate depletion of cysteine and/or cystine in the cell culture process by way of media components, batch duration, or cell density to achieve efficient production of proteins including antibody-drug-conjugates (ADCs).; conjugating a TNB-capped cysteine-containing protein by reacting it with a reducing agent capable of detaching the TNB-capping moieties from the protein without significantly reducing antibody inter-chain sulfur bonds, and conjugating reduced sulfur bonds on the protein to a payload through a reactive linking moiety.

13 Claims, 25 Drawing Sheets

(56) References Cited

FOREIGN PATENT DOCUMENTS

WO    WO2018146585 A1    8/2018

OTHER PUBLICATIONS

Sun, M., et al. "Reduction-Alkylation strategies for the Modification of Specific Monoclonal Antibody Disulfides," Bioconjug Chem., 2005, 16(5), 1282-1290.
Graham et al., "Characteristics of a Human Cell Line Transformed by DNA from Human Adenovirus Type 5", J. Gen. Virol., 1977, 36, 59-72.
Mather et al., "Culture of Testicular Cells in Hormone-Supplemented Serum-Free Medium", Annals New York Academy of Sciences, 1982, 383: 44-68.
Mather et al., "Establishment and Characterization of Two Distinct Mouse Testicular Epithelial Cell Lines", Biology of Reproduction, 1980, 23, 243-252.
Milstein et al., "Hybrid hybridomas and their use in immunohistochemistry", Nature, 1983, 305, 537-540.
Sato et al., "Cloning and Expression of a Plasma Membrane Cystine/Glutamate Exchange Transporter Composed of Two Distinct Proteins", The Journal of Biological Chemistry, 1999, 274(17): 11455-11458.
Urlaub et al., "Isolation of Chinese hamster cell mutants deficient in dihydrofolate reductase activity", Proc. Natl. Acad. Sci. USA, 1980, 77(7), 4216-4220.
International Search Report and the Written Opinion of the International Searching Authority, PCT/IB2018/050638 dated Jul. 20, 2018.
Jackson et al., "In Vitro and In Vivo Evaluation of Cysteine and Site Specific Conjugated Herceptin Antibody-Drug Conjugates", PLOSOne, 2014, 9(1), 1-14.
Duppatla et al., "Enzymatic Deglutathionylation to Generate Interleukin-4 Cysteine Muteins with Free Thiol", Bioconjugate Chemistry, 2012, 23, 1396-1405.
Sezonov et al., "*Escherichia coli* Physiology in Luria-Bertani Broth", Journal of Bacteriology, 2007, 189(23), 8746-8749.
Zhong et al., "Mechanistic understanding of the cysteine capping modifications of antibodies enables selective chemical engineering in live mammalian cells", Journal of Biotechnology, 2017, 248, 48-58.
Spens, E., et al., "Defined Protein and Animal Component-Free NS0 Fed-Batch Culture", Biotechnology and Bioengineering, (2007), vol. 98, No. 6, ISSN 0004691411, pp. 1183-1194.
Gagnon, M., et al., "High-End pH-Controlled Delivery of Glucose Effectively Suppresses Lactate Accumulation in CHO Fed-Batch Cultures", Biotechnology and Bioengineering, 2011;108: 1328-1337.

\* cited by examiner

FIG. 2A

| Run | Seed Density (E6 cells/mL) | Basal Media | | Nutrient Feed Media | | DTNB (mM) |
| --- | --- | --- | --- | --- | --- | --- |
| | | Cystine (mM) | Cysteine (mM) | Cystine (mM) | Cysteine (mM) | |
| 1_Control | 0.6 | 1.1 | 0.40 | 4.7 | 0 | 0 |
| 2 | 0.6 | 1.1 | 0.40 | 0 | 0 | 1 |
| 3 | 0.6 | 0 | 1.50 | 0 | 0 | 1 |
| 4 | 0.6 | 0.55 | 0.40 | 0 | 0 | 1 |
| 5 | 0.6 | 0 | 0.95 | 0 | 0 | 1 |
| 6 | 0.6 | 0.275 | 0.40 | 0 | 0 | 1 |
| 7 | 0.6 | 0 | 0.675 | 0 | 0 | 1 |
| 8 | 0.6 | 0 | 2.6 | 0 | 0 | 1 |

FIG. 2B
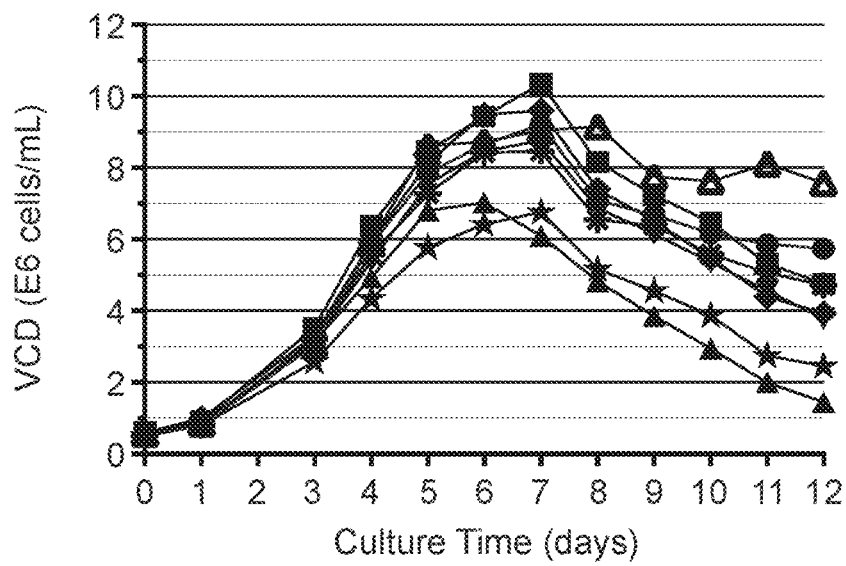
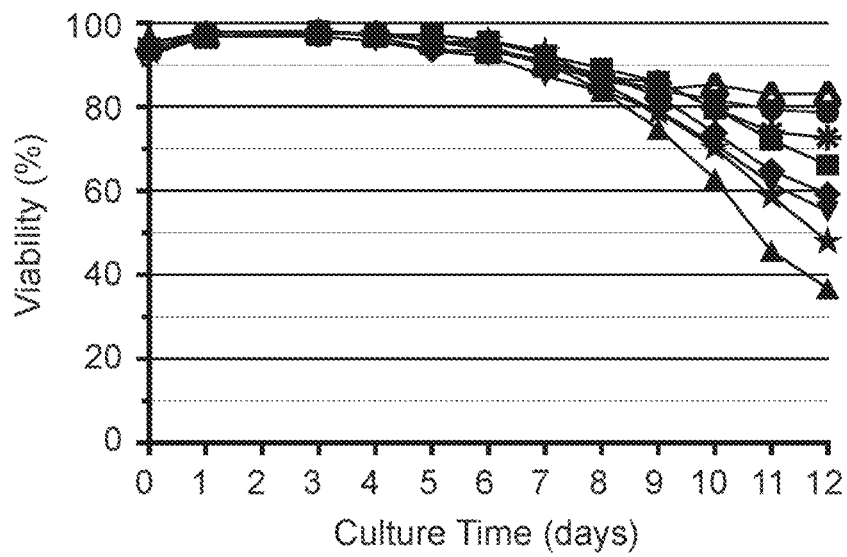
- Run 1 Control
- Run 2_1.1 mM cystine, 0.4 mM cysteine
- Run 3_1.5 mM cysteine
- Run 4_0.55 mM cystine, 0.4 mM cysteine
- Run 5_0.95 mM cysteine
- Run 6_0.275 mM cystine, 0.4 mM cysteine
- Run 7_0.675 mM cysteine
- Run 8_2.6 mM cysteine

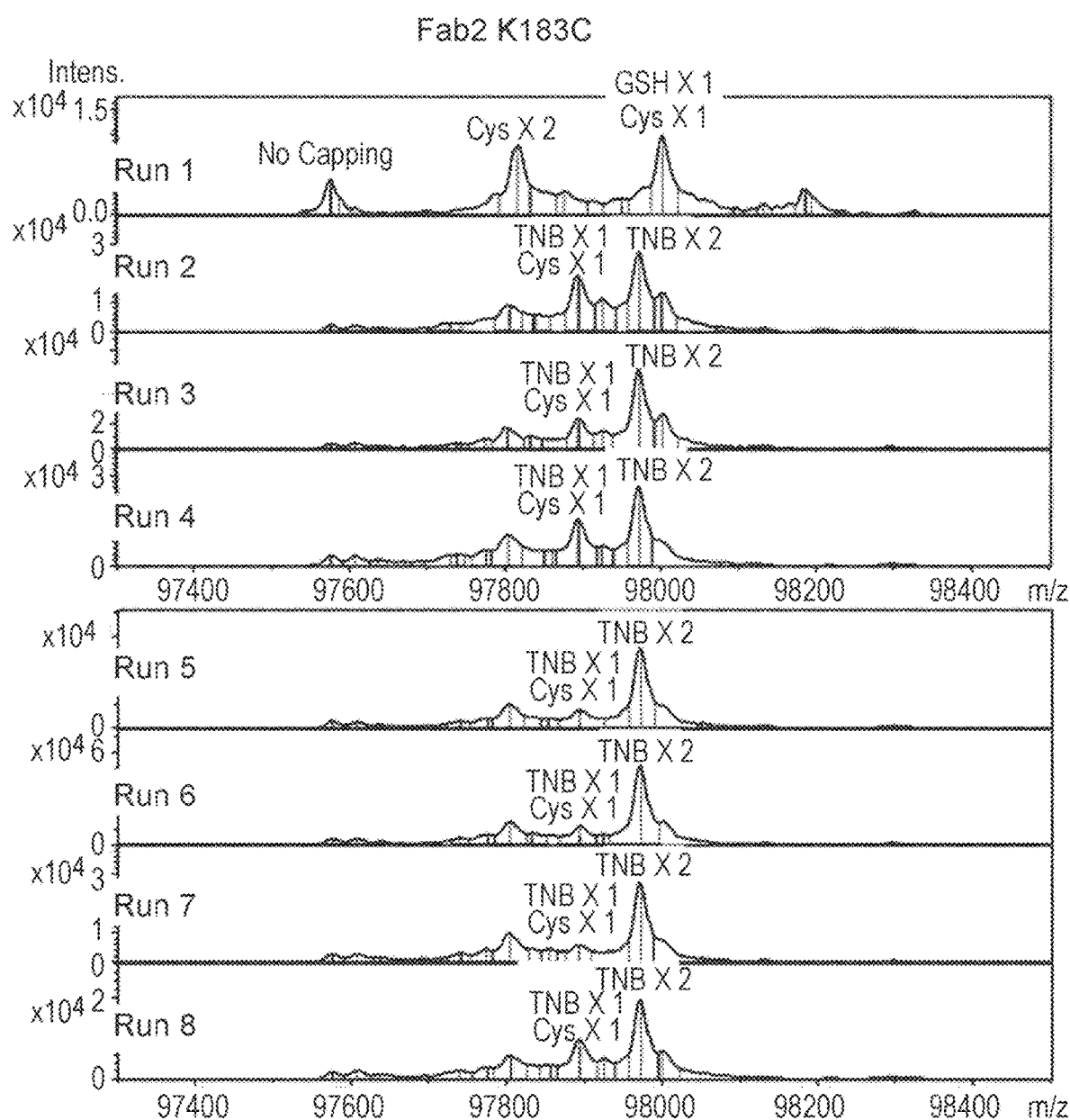

FIG. 5A

| Run | Process | Seed Density (E6 cells/mL) | Basal Media | | Nutrient Feed Media | | DTNB (mM) |
|---|---|---|---|---|---|---|---|
| | | | Cystine (mM) | Cysteine (mM) | Cystine (mM) | Cysteine (mM) | |
| 1 | HiPDOG Control | 2.0 | 1.5 | 0.4 | 4.7 | 0 | 0 |
| 3 | HiPDOG | 2.0 | 0 | 0.7 | 0 | 0 | 1 |
| 4 | HiPDOG | 2.0 | 0 | 1.0 | 0 | 0 | 1 |
| 5 | HiPDOG | 2.0 | 0.3 | 0.4 | 0 | 0 | 1 |
| 6 | HiPDOG | 2.0 | 0 | 1.3 | 0 | 0 | 1 |
| 7 | Fedbatch | 0.6 | 0 | 0.7 | 0 | 0 | 1 |
| 8 | Fedbatch Control | 0.6 | 1.1 | 0.4 | 4.7 | 0 | 0 |

FIG. 6A
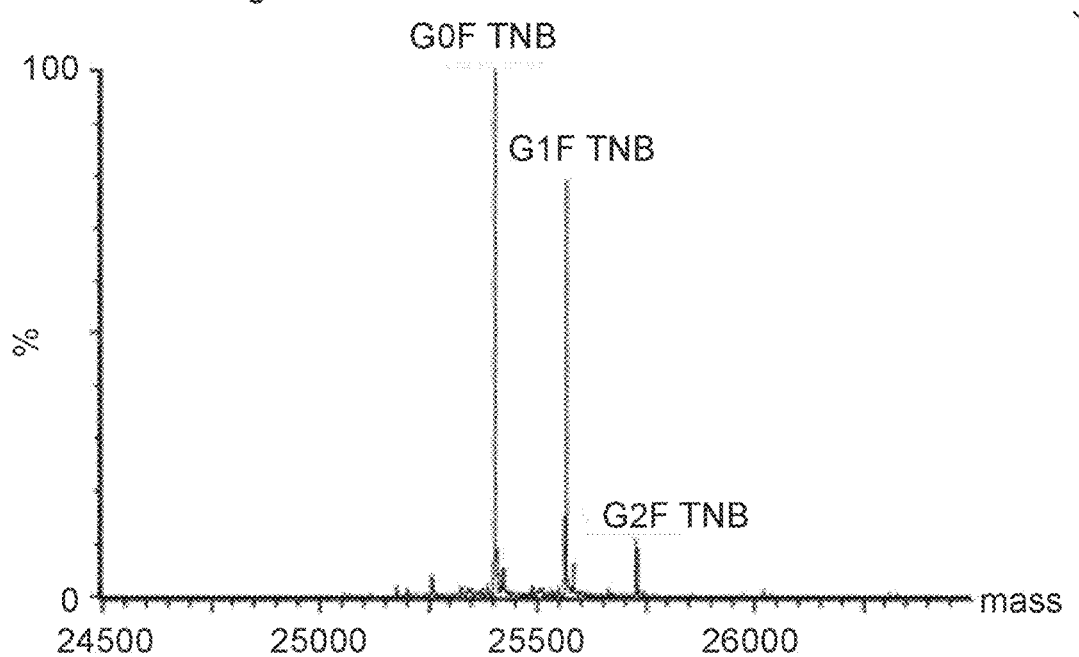
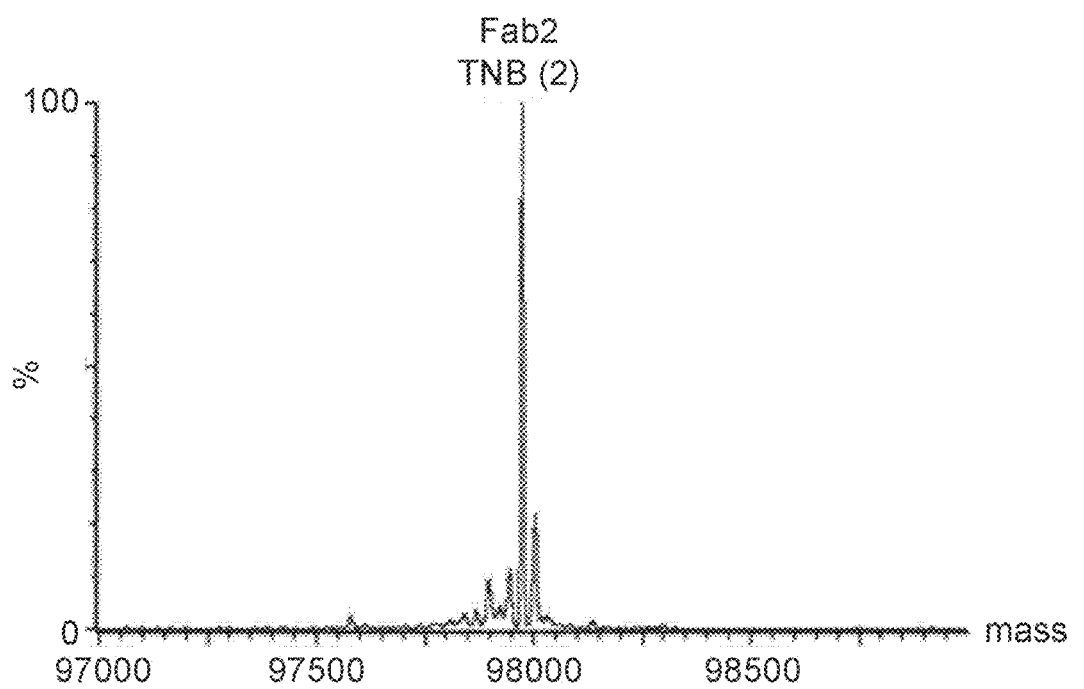

FIG. 6B

| Run | Fc K290C | | | | Fab K183C | | | |
|---|---|---|---|---|---|---|---|---|
| | Non-capping | Cys-capping | GSH-capping | TNB-capping | Non-capping | Cys-capping | GSH-capping | TNB-capping |
| 1 | 1.0 | 91.2 | 7.8 | --- | 3.4 | 96.5 | 0.1 | --- |
| 3 | 0.1 | 1.2 | 2.5 | 96.2 | 0.1 | 2.7 | 0.1 | 97.0 |
| 4 | 0.3 | 0.4 | 2.7 | 96.7 | 0.4 | 0.9 | 0.1 | 98.6 |
| 5 | 0.3 | 1.8 | 1.5 | 96.5 | 0.4 | 1.0 | 0.1 | 98.5 |
| 6 | 0.1 | 2.2 | 1.9 | 95.8 | 0.5 | 0.9 | 0.0 | 98.6 |
| 7 | 0.3 | 1.4 | 0.5 | 97.8 | 0.3 | 1.5 | 0.1 | 98.0 |
| 8 | 0.4 | 43.6 | 56.1 | --- | 16.9 | 33.6 | 49.5 | --- |

LARGE SCALE PRODUCTION PROCESS FOR CAPPED AND UN-CAPPED ANTIBODY CYSTEINES AND THEIR USE IN THERAPEUTIC PROTEIN CONJUGATION

CROSS-REFERENCE TO RELATED APPLICATIONS

This Application is the national stage filing under 35 U.S.C. 371 of Patent Cooperation Treaty Patent Application No. PCT/IB2018/050638, filed Feb. 1, 2018, which claims the benefit of priority from U.S. Provisional Application No. 62/456,293 filed Feb. 8, 2017, U.S. Provisional Application No. 62/532,262 filed Jul. 13, 2017 and U.S. Provisional Application No. 62/618,169 filed Jan. 17, 2018, the contents of each of which are hereby incorporated by reference in their entirety.

FIELD OF THE INVENTION

The field of the invention is optimizing the production of 5-thio-2-nitrobenzoate (TNB) capped cysteines on antibodies by the manipulation of cell growth conditions, allowing for more efficient production of antibody-drug-conjugates (ADCs).

BACKGROUND OF THE INVENTION

Antibody-drug-conjugates (ADCs) are a type of targeted therapy that typically consists of an antibody armed with potent cytotoxic drugs (Chudasama et al. Nature Chemistry, 2016; Junutula and Gerber, ACS medicinal chemistry letters 2016). ADCs thus offer the prospect of selective delivery of toxic payloads to tumors while avoiding off-target toxicities that often limit or exclude the use of chemotherapies from prolonged treatment periods. As a promising therapeutic platform, there are currently at least two approved ADC products on the market (brentuximab vedotin and trastuzumab emtansine). In its exponential growth, ADCs have a significant number of therapeutic candidates undergoing clinical evaluation.

In order for ADCs to achieve their therapeutic potentials, sophisticated conjugation technologies are required to connect the cytotoxic drugs to the antibody. Most of the current ADC candidates, including the two commercial ADCs, utilize conventional non-specific conjugation methods through random surface lysine or free cysteines of reduced four interchain disulfides. This generates highly heterogeneous ADC mixtures, which not only creates challenges of manufacturing reproducibility but also decreases therapeutic index significantly.

To address these issues, the ADC field has been moving towards site-specific conjugation technologies, such as cysteine (Cys) based site-specific ADCs (Junutula et al., Nat Biotechnol 2008). Robust nucleophilic thiol side chains comprising engineered unpaired cysteine residues allow a rapid and simple chemical conjugation reaction to attach diverse linkers/payloads to provide homogeneous ADC products. Better defined and improved pharmacokinetic (PK) profiles for these resulting ADC molecules have been reported. The site-specific platform has its own technical challenges. When produced in mammalian cells, thiol groups on the introduced cysteine residues form disulfides with free cysteines or glutathiones (GSH). These so-called Cys-capping modifications need to be removed prior to drug conjugation through a partial reduction step. Since such treatment also reduces the antibody inter-chain disulfides, those reduced antibody interchain disulfides must then be reformed through a re-oxidation process including dialyzing out reducing agents, cysteine or glutathione, and treating with oxidation reagents (Junutula et al., Nat Biotechnol 2008). This tedious reduction and reoxidation process potentially introduces disulfide shuffling and twisting on the antibody, which can adversely affect protein folding and protein quality, and also cause issues such as poorer PK for the resulting ADCs.

To resolve this potential issue, a novel selective reduction strategy of Cys-capping using thionitrobenzoate (TNB) has been developed (see PCT/IB2016/054789, incorporated herein by reference) without affecting inter-chain disulfides of antibody. TNB-capping, a reaction product of Ellman's reagent (5,5'-dithiobis(2-nitrobenzoate, DTNB) with free thiol group of cysteine, is a labile capping due to its weak redox potential. It has been shown that reductant tris(3-sulfonatophenyl)phosphine (TSPP) can selectively remove TNB-capping without reducing endogenous disulfides. This TNB/TSPP process followed by direct conjugation eliminates the harsh conditions of conventional reduction-reoxidation steps, keeping folding of the original antibody intact. However, more efficient methods of TNB-capping are required to optimize commercial production of ADCs.

SUMMARY OF THE INVENTION

The present invention is based on the discovery that the capping status of cysteine residues on antibodies can be modified by optimizing parameters such as cell growth, cell density and/or cell culturing. Thus the invention relates to antibody production process in mammalian cells in which engineered unpaired cysteine residues remain uncapped with free thiol, allowing for efficient modification, typically capping with thionitrobenzoate (TNB) when various concentration of dithionitrobenzoate (DTNB) are added at different cell culture stages or cell densities.

The invention further relates to antibody-drug conjugates (ADCs) or therapeutic protein drug conjugates produced using these TNB-capped antibodies, in particular ADCs formed by the selective reduction of the TNB-capped antibodies' cysteine residues, which avoids the reduction of inter-chain disulfides and thus eliminates the need for a (re)oxidation step prior to conjugation. The invention still further relates to novel thionitrobenzoate-capped antibodies made according to the methods described herein which allow for selective reduction with TSPP or related agents for direct conjugation with improved conjugation efficiency.

More specifically, in this invention it was demonstrated that the capping status of unpaired surface cysteines on an antibody can be improved by careful manipulation of cell growth, cell density, or cell culturing conditions. In mammalian cell culture, cysteine is a key amino acid. cysteine, and its oxidized form cystine (Ctn), in the culture medium is preferentially utilized for cell growth, presumably through amino acid transporter $X_c^-$ (Sato et al., J Biol Chem 1999; reproduced as FIG. 18). The Cys-capping reaction by cysteine/cystine/glutathione outside of cells is a slow process, and consequentially unpaired surface cysteines remain uncapped with free thiols during high cell density culturing. When DTNB was added to cell culture at a particular stage, nearly homogeneous TNB-capped antibody has been generated. These findings have provided a feasible strategy to produce TNB-capped antibody in large quantity.

Moreover, cell culture processes are typically designed to ensure that amino acids, such as cysteine and its equivalents are not limited or depleted, in order to maximize cell growth, viable cell density and titer and to prevent amino acid substitutions (i.e., amino acid misincorporation) (see U.S. Pat. No. 8,232,075 B). L-cysteine and its oxidized form, L-cystine, are considered key amino acids in mammalian cell culture as generation of cysteine from conversion of methionine is rate limiting for cell growth, cellular metabolism and productivity. However, in this invention several methods of deliberately limiting or depleting the amount of cysteine/cystine available to the cell culture were used to promote proper capping status of cysteine residues on the antibody with TNB.

Thus, in an embodiment of the invention there is provided a process for generating cysteine-containing proteins capable of being conjugated to a chemical payload, the process comprising the steps of: (a) seeding a cell growth medium, the medium comprising one or more growth components selected from cysteine, cystine and glutathione, with cells capable of expressing cysteine-containing proteins; (b) incubating the cells to achieve a cell density sufficient to exhaust the majority of growth components present in the growth medium; and (c) further incubating the cells to express cysteine-containing proteins having one or more uncapped cysteine residues comprising a free thiol. This process may further comprise the step of: (d) introducing a predetermined capping moiety, or a precursor thereof, to the expressed cysteine-containing proteins, whereby one or more cysteines on the protein(s) is capped with the predetermined capping moiety. In this embodiment achieved cell density is typically at least about 1 E6 cells/mL, and may be for example, at least about: 5E6 cells/mL, 10E6 cells/mL, 50E6 cells/mL, 100E6 cells/mL or 500E6 cells/mL, preferably above 10E6 cells/mL, more preferably above 50E6 cells/mL.

Note that the predetermined capping moiety may be an alkylating agent, in some instances acting as chemical "handles" other than TNB or similar labile moieties useful for additional types of drug conjugation chemistry. These handles are appended to the antibody by adding novel alkylating chemical spacers into the culture medium. The alkylating chemical spacers contain chemical handles such as aldehydes, ketones, azides, and alkynes. In the case of ketones and aldehydes, these chemical handles can react with aminooxy nucleophiles or hydrazide for additional conjugation chemistry, forming oxime/hydrazone products. In the case of azides and alkynes, these chemical handles can permit cycloaddition conjugation. Additional alkylating chemical spacers includes functional domain of Biotin, which allows specific tight non-covalent interaction between Strepavidin and Biotin. See WO2017/025897 at Example 4 which discusses the chemical handle maleimido trioxa-4-formyl benzamide (MTFB), dibenzocyclooctyl-polyethylene maleimide (DBCO-PEG4-Maleimide), and Maleimide-PEG2-Biotin (MPB).

A further embodiment of the invention includes a process for generating cysteine-containing proteins capable of being conjugated to a chemical payload, the process comprising the steps of: (a) seeding a cell growth medium, the medium comprising one or more growth components selected from cysteine, cystine and glutathione, with cells capable of expressing cysteine-containing proteins; (b) incubating the cells to express cysteine-containing proteins having one or more uncapped cysteine residues comprising a free thiol; and (c) in step (a), step (b) or both steps (a) and (b), maintaining the concentration of the one or more growth components at concentrations below 0.4 mM, below 0.3 mM, below 0.2 mM, below 0.1 mM or below 0.05 mM. This process may further comprise the step of: (d) introducing a predetermined capping moiety, or a precursor thereof, to the expressed cysteine-containing proteins, whereby one or more cysteines on the proteins are capped with the predetermined capping moiety.

A still further embodiment includes a process for generating cysteine-containing proteins capable of being conjugated to a chemical payload, the process comprising the steps of: (a) seeding a cell growth medium, the medium comprising one or more growth components selected from cysteine, cystine and glutathione, with cells capable of expressing cysteine-containing proteins, including but not limited to where the initial concentration of the growth components is below 2 mM, below 0.4 mM, below 0.3 mM, below 0.2 mM, below 0.1 mM or below 0.05 mM, and then (b) incubating the cells to express cysteine-containing proteins having one or more uncapped cysteine residues comprising a free thiol. This process may further comprise the step of: (c) introducing a predetermined capping moiety, or a precursor thereof, to the expressed cysteine-containing proteins, whereby one or more cysteines on the proteins are capped with the predetermined capping moiety.

Also within the present invention are embodiments where growth components are exhausted in the cell culture by deliberately limiting the cysteine and/or its alternative forms in the process. Using rational media design and stoichiometric approaches taught in U.S. Pat. No. 8,232,075 B, the required amount of cysteine/cystine needed for a particular peak cell density and amount of product produced can be calculated by the equation below (Equation 1). This equation is generic for CHO cultures and a more specific equation can be generated for a particular cell line by determining the cysteine consumption rate for that cell line in a given process.

Equation 1. Required Cysteine Concentration $$\text{Required Cysteine Concentration} = [(x*m) + (x*m*k) + (p*n)]*f$$

x: cysteine concentration required for E6 cells/mL (0.09 mM)
m: peak cell density (E6 cells/mL)
k: maintenance factor (10-15%)
p: cysteine concentration required for 1 g/L antibody (0.19 mM)
n: final antibody concentration (1 g/L)
f: safety factor (1.1-1.3)

After determining the require amount of cysteine for a particular cell line in a given process, the fractional cysteine limitation ratio equation can be used to determine the amount of cysteine/cystine to provide in a process to target a specific limitation ratio (Equation 2), in order to deliberately limit or deplete the cysteine/cystine in the culture. Within the present invention are embodiments where growth components are exhausted by limiting the fractional cysteine limitation ratio in the cell growth medium to less than about 1.0×. These ratios may be, for instance, about: 0.95×, 0.90×, 0.85×, 0.80×, 0.75×, 0.70×, 0.65×, 0.60×, 0.55×, 0.50×, 0.45×, 0.40×, 0.35×, 0.30×, 0.25×, 0.20×, 0.15×, 0.10× or 0.05×.

Fractional Cysteine Limitation Ratio $$\text{Fraction Cysteine Limitation Ratio} = \frac{\text{Cysteine Provided in Process}}{\text{Required Cysteine from Equation 1}} \quad \text{Equation 2}$$

Of course, the cysteine-containing proteins of the invention include a wide variety of moieties, including but not limited to antibodies and fusion proteins. These may be an anti-EDB antibody and an anti-HER2 antibody including trastuzumab.

In the processes described herein, the predetermined capping moiety may be selected from the group consisting of 5-thio-2-nitrobenzoic acid (TNB), 2-mercaptopyridine, dithiodipyridine (DTDP), 4-thiobenzoic acid, 2-thiobenzoic acid, 4-thiobenzenesulfonic acid, 2-thiobenzenesulfonic acid, methyl sulfonate (Ms), p-toluenesulfonate (Ts) and trifluoromethanesulfonate (Tf); and/or the predetermined capping moiety is selected from a reactive group consisting of maleimido trioxa-4-formyl benzamide (MTFB) like molecules with an aldehyde handle or maleimido azido-lysine-like molecules with an azide handle, or dibenzocyclooctyl-polyethylene maleimide (DBCO-PEG4-Maleimide)-like molecules with an alkyne handle. Often, the predetermined capping moiety is TNB, and often the precursor is DTNB.

Also in the processes described herein, the capped proteins are subject to further processing consisting of one or more of isolation, purification and concentration, at one or more different points in the process. Thus in certain embodiments of the invention at least 50% of the cells are separated from the expressed cysteine-containing proteins prior to introduction of the predetermined capping moiety or precursor thereof. This separation may be accomplished by centrifugation or filtration.

The invention further provides embodiments for conjugating a TNB-capped (or otherwise capped) cysteine-containing protein, comprising the steps of: (a) reacting the TNB-capped cysteine-containing protein with a reducing agent capable of detaching the TNB-capping moieties from the protein without significantly reducing antibody inter-chain sulfur bonds; (b) filtering the reaction mixture to remove excess reducing agent, detached TNB, or both; and (c) without introducing an oxidizing agent, conjugating one or more reduced sulfur bonds on the antibody to a payload through a reactive linking moiety.

The invention still further provides embodiments for conjugating a TNB-capped (or otherwise capped) cysteine-containing protein, comprising the steps of: (a) reacting the TNB-capped cysteine-containing protein with stoichiometric excess of reducing agent capable of detaching the TNB-capping moieties from the protein without significantly reducing antibody inter-chain sulfur bonds, optionally in the presence of salts such as sodium chloride or other salts (see Example 8); (b) filtering the reaction mixture to remove one or more of excess reducing agent, detached TNB; (c) introducing an oxidizing agent to repair reduced inter-chain sulfur bonds caused by excess reducing agent; and (d) conjugating one or more reduced sulfur bonds on the antibody to a payload through a reactive linking moiety. The stoichiometric excess is typically about 4:1 to 6:1 reducing agent to capped cysteine residue (for instance, 16:1 to 24:1 reducing agent to antibody for an antibody with four capped cysteines), and preferably about 5:1. Step (c) of this process can be performed at ambient temperatures, for instance at about 25 degrees Celsius, in order to shorten oxidation times and to avoid process temperature changes. Performance at low temperatures, for example at about 4 degrees Celsius, requires longer oxidation time, but is less sensitive to loss of yield if target oxidation time is exceeded. The above described process may further comprise a step of: (e) adding excess cysteine after step (d) to quench the reaction of the linking moiety; and (f) separating the quenched linker-payload from the conjugate. The cysteine quench allows for improved separation of linker-payload by chromatography or diafiltration. Further, in the above-described process the separation may be performed by diafiltration or column chromatography, typically hydrophobic interaction chromatography (HIC). Use of isopropanol-containing buffers to perform the HIC purification results in increased recovery of purified conjugate.

DESCRIPTION OF THE FIGURES

FIG. 2. High cell density culture conditions of a stable CHO cell line in CHO medium with DTNB. CHO-K1 cells, stably expressing trastuzumab cysteine mutant K183C-K290C, were seeded in proprietary basal medium with the density of 0.6E6 cells/mL in a controlled fed-batch bioreactor as described in Example 1. Panel A shows culture conditions of basal media, feed media, or DTNB. Panel B shows viable cell density (VCD) and culture viability.

FIG. 4. Fully TNB-capped cysteine mutant antibody at Fab K183C site was generated by high cell density of stable CHO expression in CHO medium with DTNB. Conditioned media from culture conditions described in FIG. 2 was purified through ProA column/SEC and the antibody trastuzumab cysteine mutant K183C-K290C were digested with IDES and subjected to LC/MS analysis as described in Example 1.

FIG. 6. Fully uncapped cysteine mutant antibody was generated by high cell density of stable CHO expression in CHO medium with DTNB. Conditioned media from culture conditions described in FIG. 5 was purified through ProA column/SEC and the antibody trastuzumab cysteine mutant K183C-K290C were digested with IDES and subjected to LC/MS analysis (Panel A). Panel B shows the capping data summary table.

DETAILED DESCRIPTION OF THE INVENTION

Figure 1:
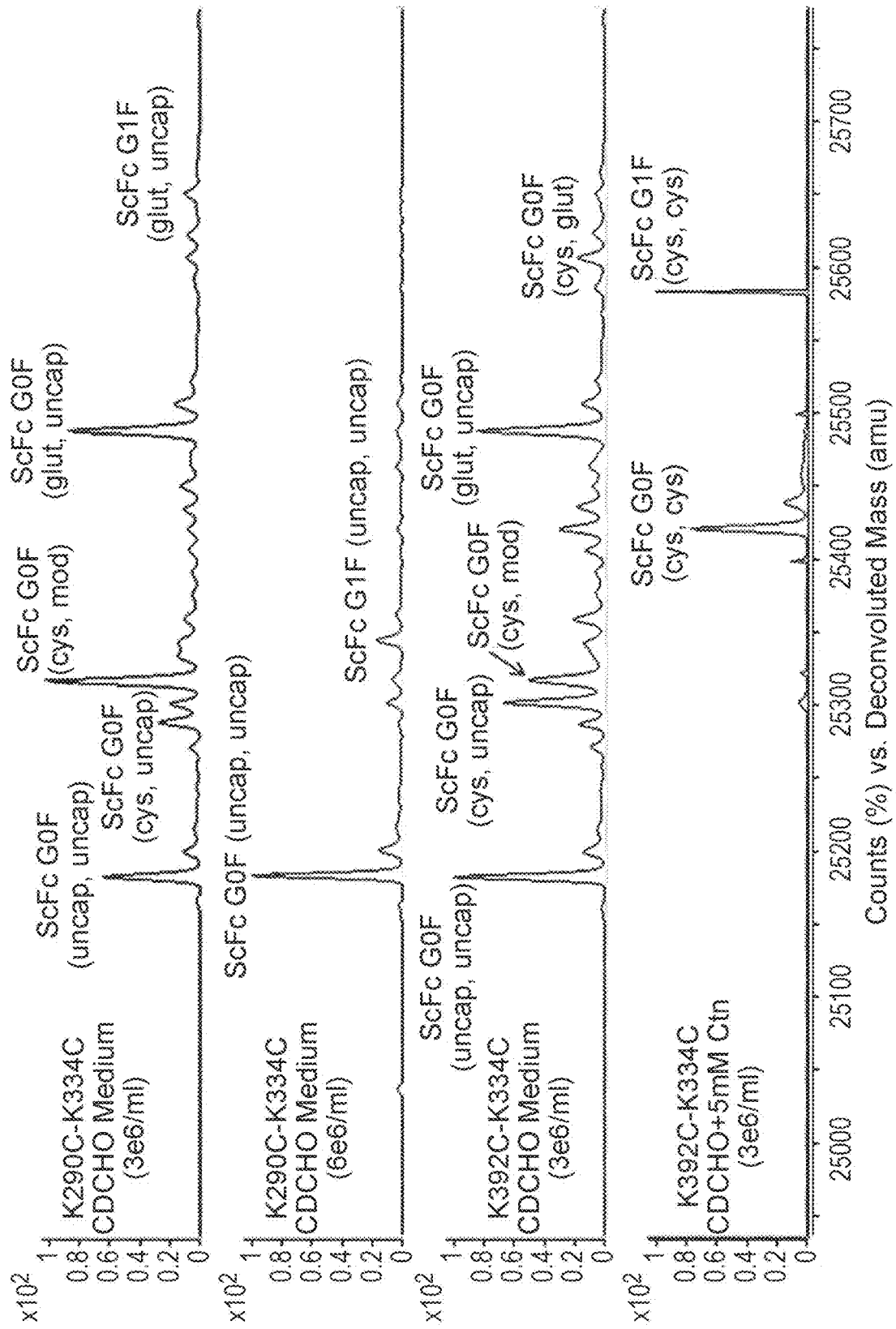
FIG. 1. Fully uncapped cysteine mutant antibody was generated by high cell density of stable CHO expression in regular CD CHO medium. CHO-K1 cells, stably expressing trastuzumab cysteine mutant K290C-K334C or K392C-K334C, were seeded in CD CHO medium with the density of 3E6 cells/ml or 6E6 cells/ml, and cultured for 72 hours at 37 degrees Celsius. Conditioned media were purified through ProA column and size-exclusion column (SEC). Purified antibody proteins were subjected to LC/MS analysis as described in Example 1.

General Procedures
Cell Culture Methods

The terms "culture" and "cell culture" as used herein refer to a cell population that is suspended in a medium under conditions suitable to survival and/or growth of the cell population. As will be clear to those of ordinary skill in the art, in some embodiments, these terms as used herein refer to the combination comprising the cell population and the medium in which the population is suspended. In some embodiments, the cells of the cell culture comprise mammalian cells.

The present invention may be used with any cell culture method that is amenable to the desired process (e.g., production of a recombinant protein (e.g., antibody)). As a non-limiting example, cells may be grown in batch or fed-batch cultures, where the culture is terminated after sufficient expression of the recombinant protein (e.g., antibody), after which the expressed protein (e.g., antibody) is harvested. Alternatively, as another non-limiting example, cells may be grown in batch-refeed, where the culture is not terminated and new nutrients and other components are periodically or continuously added to the culture, during which the expressed recombinant protein (e.g., antibody) is harvested periodically or continuously. Other suitable methods (e.g., spin-tube cultures) are known in the art and can be used to practice the present invention.

In some embodiments, a cell culture suitable for the present invention is a fed-batch culture. The term "fed-batch culture" as used herein refers to a method of culturing cells in which additional components are provided to the culture at a time or times subsequent to the beginning of the culture process. Such provided components typically comprise nutritional components for the cells which have been depleted during the culturing process. A fed-batch culture is typically stopped at some point and the cells and/or components in the medium are harvested and optionally purified. In some embodiments, the fed-batch culture comprises a base medium supplemented with feed media. In some embodiments lactate is maintained at low levels by using the high-end pH-controlled delivery of glucose (HiPDOG process) disclosed in Gagnon et al.

In some embodiments, a cell culture suitable for the present invention is a perfusion process. The term "perfusion" as used herein refers to a method of culturing cells in which cells receive inoculation base medium, and at the point when cells achieve a desired cell density, cell perfusion is initiated such that the spent medium is replaced by fresh medium. The perfusion process allows the culture to achieve high cell density, and thus enables the production of a large quantity of product. However, at least some forms of the perfusion process require supplying a large quantity of medium and result in some portion of the product being contained in a large volume of spent medium rather than being concentrated in a single harvest.

The term "bioreactor" as used herein refers to any vessel used for the growth of a prokaryotic or eukaryotic cell culture (e.g., a mammalian cell culture). The bioreactor can be of any size as long as it is useful for the culturing of cells (e.g., mammalian cells). Cells may be grown in any convenient volume chosen by the practitioner. For example, cells may be grown in small scale reaction vessels ranging in volume from a few milliliters to several liters. Alternatively, cells may be grown in large scale commercial Bioreactors ranging in volume from approximately at least 1 liter to 10, 50, 100, 250, 500, 1000, 2500, 5000, 8000, 10000, 12000, 15000, 20000 or 25000 liters or more, or any volume in between.

In some embodiments, the cells may be grown during the initial growth phase (or growth phase) for a greater or lesser amount of time, depending on the needs of the practitioner and the requirement of the cells themselves. In some embodiments, the cells are grown for a period of time sufficient to achieve a predefined cell density. In some embodiments, the cells are grown for a period of time sufficient to achieve a cell density that is a given percentage of the maximal cell density that the cells would eventually reach if allowed to grow undisturbed. For example, the cells may be grown for a period of time sufficient to achieve a desired viable cell density of 1, 5, 10, 15, 20, 25, 30, 35, 40, 45, 50, 55, 60, 65, 70, 75, 80, 85, 90, 95 or 99 percent of maximal cell density. In some embodiments, the cells are grown until the cell density does not increase by more than 15%, 14%, 13%, 12%, 11%, 10%, 9%, 8%, 7%, 6%, 5%, 4%, 3%, 2% or 1% per day of culture. In some embodiments, the cells are grown until the cell density does not increase by more than 5% per day of culture.

In some embodiment the cells are allowed to grow for a defined period of time. For example, depending on the starting concentration of the cell culture, the temperature at which the cells are grown, and the intrinsic growth rate of the cells, the cells may be grown for 0, 1, 2, 3, 4, 5, 6, 7, 8, 9, 10, 11, 12, 13, 14, 15, 16, 17, 18, 19, 20 or more days, preferably for 4 to 10 days. In some cases, the cells may be allowed to grow for a month or more. The practitioner of the present invention will be able to choose the duration of the initial growth phase depending on protein production requirements and the needs of the cells themselves.

In some embodiments, the cells may be maintained in the subsequent production phase until a desired cell density or production titer is reached. In another embodiment of the present invention, the cells are allowed to grow for a defined period of time during the subsequent production phase. For example, depending on the concentration of the cell culture at the start of the subsequent growth phase, the temperature at which the cells are grown, and the intrinsic growth rate of the cells, the cells may be grown for 1, 2, 3, 4, 5, 6, 7, 8, 9, 10, 11, 12, 13, 14, 15, 16, 17, 18, 19, 20 or more days. In some cases, the cells may be allowed to grow for a month or more. The practitioner of the present invention will be able to choose the duration of the subsequent production phase depending on polypeptide or protein production requirements and the needs of the cells themselves.

In some embodiments, the cells express a recombinant protein and the cell culture method of the invention comprises a growth phase and a production phase.

Cells

Any cell susceptible to cell culture may be utilized in accordance with the present invention. In some embodiments, the cell is a mammalian cell. Non-limiting examples of mammalian cells that may be used in accordance with the present invention include BALB/c mouse myeloma line (NSO/I, ECACC No: 85110503); human retinoblasts (PER.C6, CruCell, Leiden, The Netherlands); monkey kidney CV1 line transformed by SV40 (COS-7, ATCC CRL 1651); human embryonic kidney line (293 or 293 cells subcloned for growth in suspension culture, Graham et al., J. Gen Virol., 36:59, 1977); baby hamster kidney cells (BHK, ATCC CCL 10); Chinese hamster ovary cells+/− DHFR (CHO, Urlaub and Chasin, Proc. Natl. Acad. Sci. USA, 77:4216, 1980); mouse sertoli cells (TM4, Mather, Biol. Reprod., 23:243-251, 1980); monkey kidney cells (CV1 ATCC CCL 70); African green monkey kidney cells (VERO-76, ATCC CRL-1 587); human cervical carcinoma cells (HeLa, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci., 383:44-68, 1982); MRC 5 cells; FS4 cells; and a human hepatoma line (Hep G2). In some preferred embodiment, the cells are CHO cells. In some preferred embodiments, the cells employ the glutamine synthetase (GS) gene expression system.

Additionally, any number of commercially and non-commercially available hybridoma cell lines may be utilized in accordance with the present invention. The term "hybridoma" as used herein refers to a cell or progeny of a cell resulting from fusion of an immortalized cell and an antibody-producing cell. Such a resulting hybridoma is an immortalized cell that produces antibodies. Individual cells used to create the hybridoma can be from any mammalian source, including, but not limited to, rat, pig, rabbit, sheep, pig, goat, and human. In some embodiments, a hybridoma is a trioma cell line, which results when progeny of heterohybrid myeloma fusions, which are the product of a fusion between human cells and a murine myeloma cell line, are subsequently fused with a plasma cell. In some embodiments, a hybridoma is any immortalized hybrid cell line that produces antibodies such as, for example, quadromas (See, e.g., Milstein et al., Nature, 537:3053, 1983). One skilled in the art will appreciate that hybridoma cell lines might have different nutrition requirements and/or might require different culture conditions for optimal growth, and will be able to modify conditions as needed.

Cell Growth and Productivity

High cell density as used herein refers to cell density above 1E6 cells/mL, 5E6 cells/mL, 10E6 cells/mL, 50E6 cells/mL, 100E6 cells/mL or 500E6 cells/mL, preferably above 10E6 cells/mL, more preferably above 50E6 cells/mL.

In some embodiments, cell growth is determined by viable cell density (VCD), maximum viable cell density, or integrated viable cell count (IVCC). In some embodiments, cell growth is determined by maximum viable cell density.

The term "viable cell density" as used herein refers to the number of cells present in a given volume of medium. Viable cell density can be measured by any method known to the skilled person. Preferably, viable cell density is measured using an automated cell counter such as Bioprofile Flex® (Nova Biomedical, Waltham, MA). The term maximum cell density as used herein refers to the maximum cell density achieved during the cell culture. The term "cell viability" as used herein refers to the ability of cells in culture to survive under a given set of culture conditions or experimental variations. Those of ordinary skill in the art will appreciate that one of many methods for determining cell viability are encompassed in this invention. For example, one may use a dye (e.g., trypan blue) that does not pass through the membrane of a living cell, but can pass through the disrupted membrane of a dead or dying cell in order to determine cell viability.

The term "integrated viable cell count (IVCC)" as used herein refers to as the area under the viable cell density (VCD) curve. IVCC can be calculated using the following formula:

$$IVCC_{t+1} = IVCC_t + (VCD_t + VCD_{t+1}) * (\Delta t)/2$$

where $\Delta t$ is the time difference between t and t+1 time points. $IVCC_{t=0}$ can be assumed negligible. $VCD_t$ and $VCD_{t+1}$ are viable cell densities at t and t+1 time points.

In some embodiments of the above described methods, the productivity is determined by titer and/or volumetric productivity.

The term "titer" as used herein refers, for example, to the total amount of recombinantly expressed protein produced by a cell culture in a given amount of medium volume. Titer is typically expressed in units of grams of protein per liter of medium.

In some embodiments of the above described methods, the productivity is determined by titer. In some embodiments, the productivity is increased by at least 5%, 10%, 15%, 20% or 25% as compared to the control culture. In some embodiments, the productivity is increased by at least 10% as compared to a control culture. In some embodiments, the productivity is increased by at least 20% as compared to a control culture.

Cell Culture Media

The terms "medium", "cell culture medium" and "culture medium" as used herein refer to a solution containing components or nutrients which nourish growing mammalian cells. Typically, the nutrients include essential and non-essential amino acids, vitamins, energy sources, lipids, and trace elements required by the cell for minimal growth and/or survival. Such a solution may also contain further nutrients or supplementary components that enhance growth and/or survival above the minimal rate, including, but not limited to, hormones and/or other growth factors, particular ions (such as sodium, chloride, calcium, magnesium, and phosphate), buffers, vitamins, nucleosides or nucleotides, trace elements (inorganic compounds usually present at very low final concentrations), inorganic compounds present at high final concentrations (e.g., iron), amino acids, lipids, and/or glucose or other energy source. In some embodiments, a medium is advantageously formulated to a pH and salt concentration optimal for cell survival and proliferation. In some embodiments, a medium is a feed medium that is added after the beginning of the cell culture.

Methods for Measuring the Amino Acid Concentration

The concentration of amino acid can be measured by any method known to the skilled person. Preferred methods to measure the concentration of amino acids in online or offline methods include for example Liquid Chromatography such HPLC, UPLC or LCMS, NMR or GCMS.

In some embodiments, the concentration of amino acid is measured off line by taking a sample of the cell culture medium and measuring the concentration of said at least one amino acid in said sample. In some embodiments, the concentration of amino acid is measured as disclosed in Examples 3.1, 3.2, and 3.3. A preferred method to measure the concentration of amino acids in an off line method is UPLC.

In some embodiments, the concentration of amino acid is measured online. In some embodiments, the concentration of amino acid is measured on-line using Raman spectroscopy. In some embodiments, the concentration of amino acid is measured on-line using Raman spectroscopy. In some embodiments, the concentration of amino acid is measured online using HPLC or UPLC based technology with an auto-sampler that draws sample from reactor and transfers to the equipment in a programmed manner.

Additional procedures as described in WO2015/140708 may also be employed in the present invention, and are incorporated by reference herein.

Methods for Measuring the Drug-to-Antibody Ratio

The drug-to-antibody ratio (DAR) can be measured by any method known to the skilled person. Preferred methods to measure the DAR include, for example, liquid chromatography such HPLC, UPLC or LCMS, mass spectrometry, and NMR.

In some embodiments, the DAR is measured by taking a sample of the conjugation mixture, chromatography fraction, or further purified material and measuring the concentration of said in said sample. Preferred methods to measure the DAR are hydrophobic interaction chromatography (HIC HPLC) and reverse-phase HPLC.

Additional Definitions

Additional to the definitions provided above, the following additional definitions are provided:

CHO is described herein as Chinese hamster ovary (CHO) cells which are derived from the ovary of the Chinese hamster used for production of therapeutic proteins, as disclosed in the examples provided. CHO-K1 is described herein as the ancestral host cell line subcloned from the parental CHO cell line comprising of a glutamine synthase (GS) expression system commercially available from Lonza.

HiPDOG as used herein refers to "High-end pH-controlled delivery of glucose" (HiPDOG) is a nutrient feeding method that delivers a concentrated glucose solution triggered by rising pH to suppress lactate accumulation in cell culture.

The term mAb as used herein refers to monoclonal antibody.

Figure 19:
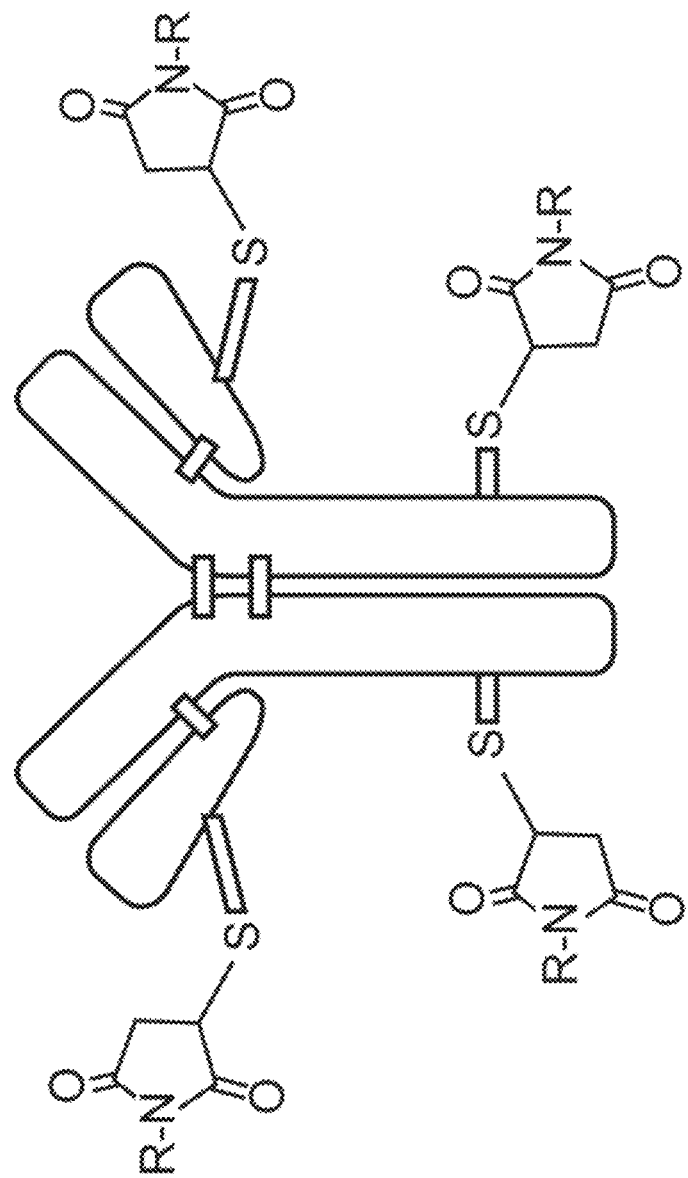
FIG. 19. A schematic representation of an example of a drug-to-antibody ratio of 4:1 is depicted, in which four drug payloads are linked to one protein. "R" represents the payload.

The term DAR4 as used herein refers to the drug-to-antibody ratio of 4:1, in which four drug payloads are linked to one protein (for example, see FIG. 19 which depicts one such instance where "R" represents the payload). The term crude DAR4 describes the drug-to-antibody ratio after the conjugation process but prior to the final purification step.

The term UF/DF as used herein refers to ultrafiltration/diafiltration.

EXAMPLES

The following Examples illustrate important features of the invention.

Example 1: Generation of Fully Uncapped Cysteine Mutant Antibodies by High Cell Density of Stable CHO Expression in Regular CD CHO Medium CHO-K1 cells stably expressing the cysteine mutant antibody trastuzumab K290C-K334C or K392C-K334C, were seeded in regular CD CHO medium (Thermo Fisher, Waltham, MA) with the density of 3E6 cells/mL or 6E6 cells/mL, were grown and maintained in a humidified incubator with 5% $CO_2$ at 37 degrees Celsius. In one condition, 5 mM cystine was added to the CD CHO medium. Cells were cultured for 72 hours at 37 degrees Celsius. Cell viability was measured and conditioned media were harvested. Cells were more than 98% viable.

Antibody protein was purified through ProA and size-exclusion columns as follows. Conditioned media were filtered with 0.2 μm filters and passed through Protein A resin (GE Healthcare, Piscataway, NJ) pre-equilibrated with 50 mM Tris, 150 mM NaCl, pH 7.5 (TBS). The column was washed with 2 column volumes (CV) of TBS, 5CVs of $CaCl_2$, pH 7.5, 3CVs of 10 mM Tris, 10 mM NaCl, pH 7.5, before the protein was eluted using 100% step of 150 mM Glycine, 40 mM NaCl, pH 3.5. The protein was adjusted to the pH to 7.0 using 2M HEPES, pH 8.0, and the protein was loaded onto a Superdex 200 column equilibrated with PBS (137 mM NaCl, 2.7 mM KCl, 8.1 mM $Na_2HPO_4$, 2.7 mM $KH_2PO_4$, pH 7.2). Peak fractions were pooled concentrated to 10 mg/mL using a 50 kDa MWCO centrifugal device.

The protein samples were analyzed by mass spectrometry for Cys-capping status measurement as follows. Liquid chromatography mass spectrometry (LC/MS) analysis was performed using a Waters Xevo Q-TOF G2 mass spectrometer (Waters, Milford, MA) coupled to an Agilent (Santa Clara, CA) 1200 capillary HPLC. Protein samples were treated with IdeS protease (Promega, Madison, WI) at room temperature for 2 hrs. Protein samples were acidified by diluting 1:1 with 0.05% TFA (Sigma-Aldrich, St Louis, MO), followed by liquid chromatography mass spectrometry analysis. The samples were separated over a Waters BEH300 C4, 1.7 μm (1.0×50 mm) column maintained at 80° C. with a flow rate of 65 μl/min. Mobile phase A was water with 0.05% TFA, and mobile phase B was acetonitrile with 0.05% TFA. Proteins were eluted from the column using a gradient: 2% to 20% B in 0.5 min, 20% to 40% B in 6 min, and 40% to 100% B in 4 min. The mass spectrometer was run in positive MS only mode scanning from 800 to 3500 m/z and data was acquired with MassLynx (Waters) 4.1 software. The TOF-MS signal corresponding to the antibody were summarized and deconvoluted using MaxEnt1 (Waters) program. Cysteine and glutathione capped species were determined by mass shift (Cys: 119.004 Da, GSH: 305.068 Da).

As shown in FIG. 1, for CD CHO medium, the cysteine mutant antibody was fully cysteinylated when 5 mM cystine was added to the medium. In the regular CD CHO medium, CHO cells produced substantial uncapped cysteine mutant protein at the cell density of 3E6 cells/mL. When the CHO cells were increased to 6E6 cells/mL, fully uncapped cysteine mutant antibody was generated, suggesting that most cystine in the medium was used for cell growth. The increase of cell density could deplete medium of cystine and consequently affect the capping status of unpaired surface cysteines.

Example 2: Generation of Fully TNB-Capped Cysteine Mutant Antibodies by High Cell Density of Stable CHO in Regular CHO Medium As shown in Example 1, cell growth at high density could consume significant amounts of cysteine or cystine in the medium. Fully uncapped cysteine mutant antibody was consequently generated. Building on Example 1, this allowed generation of fully TNB-capped cysteine mutant antibodies in large quantity by adding various concentrations of DTNB to cell culture at different time points. DTNB efficiently alkylated free thiols on uncapped mutant antibodies, resulting in the generation of TNB-capped antibodies.

Thus, CHO cell lines stably expressing cysteine mutant antibody trastuzumab K183C-K290C were seeded into a controlled bioreactor (Applikon, Inc., Schiedam, Netherlands) with a 1 L initial working volume. As shown, eight conditions were run evaluating different concentrations of cysteine and/or cystine in the basal media, as show in FIG. 2A. The fed-batch culture process was seeded at 0.6E6 cells/mL and controlled with fixed percentage nutrient feeds based on culture volume and was administered starting day 3; conditions producing TNB-capped antibodies used feed media that was free of both cysteine and cystine. On day 7, 1 mM DTNB was added to the culture and the cell culture was continued for an additional five days.

As shown in FIG. 2B, cell doubling and viability were normal under all conditions tested.

Figure 3A:
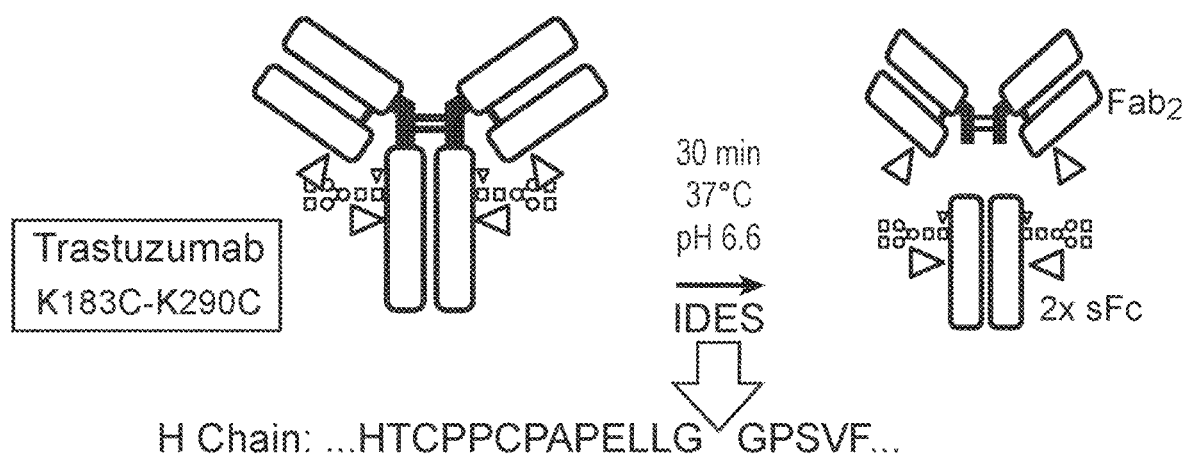
FIG. 3. Fully TNB-capped cysteine mutant antibody at Fc K290C site was generated by high cell density of stable CHO expression in CHO medium with DTNB. Conditioned media from culture conditions described in FIG. 2 was purified through ProA column/SEC and the antibody trastuzumab cysteine mutant K183C-K290C were digested with IDES (Panel A) and subjected to LC/MS analysis as described in Example 1.
Figure 3B:
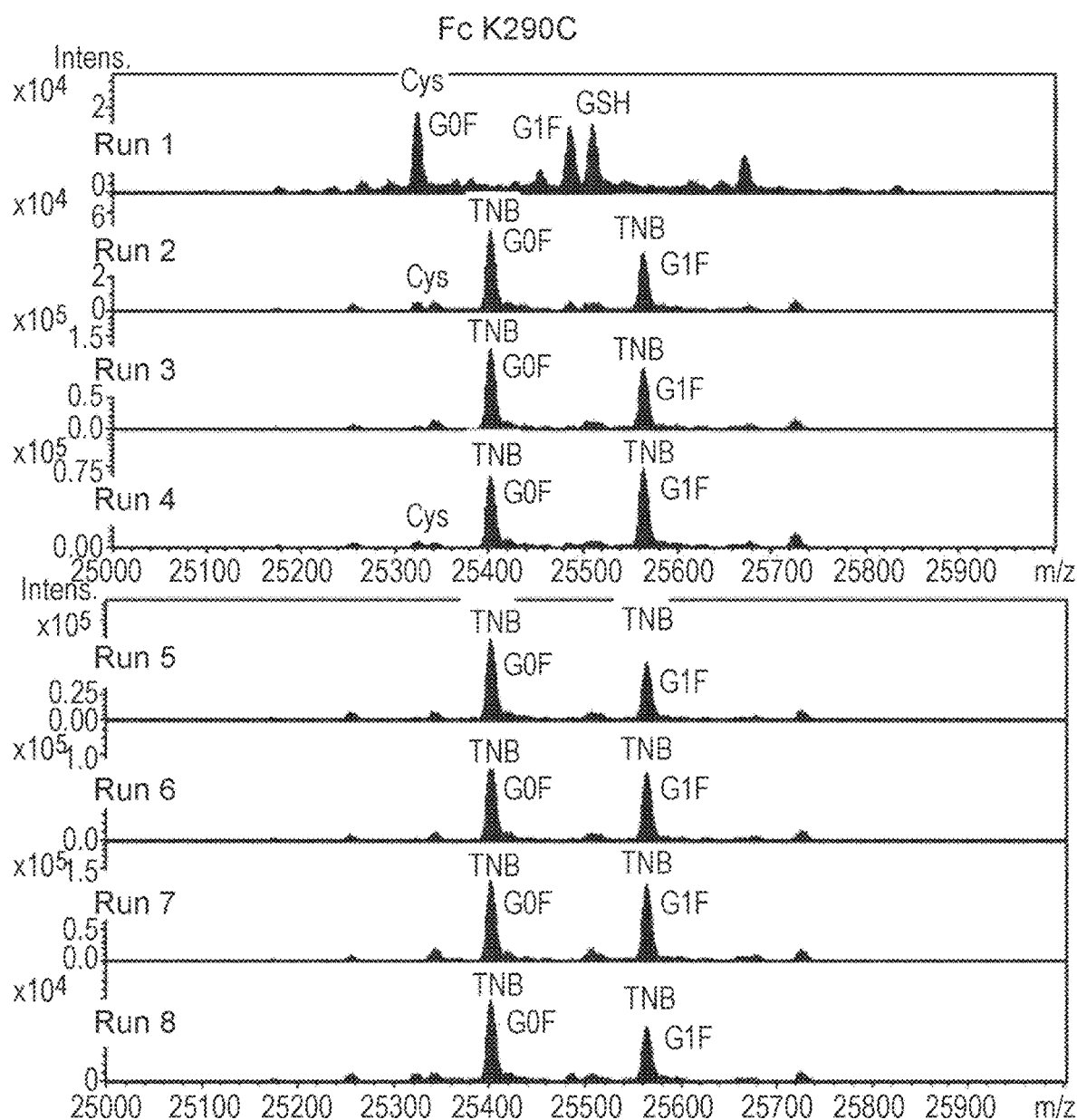

When the antibody proteins were purified, they were subjected to Cys-capping analysis. As shown in FIG. 3A, antibody was digested by Ides protease to generate Fc fragment and Fab2 fragment. The mixture was analyzed by LC/MS as described in Example 1 above. As shown in FIG. 3B, for the less-solvent-exposed Fc-located K290C site, all TNB-added conditions (Runs 2-8) produced >95% TNB-capped materials. As shown in FIG. 4, for the more solvent-exposed light chain-located Fab K183C site, TNB-added conditions (Runs 5-8) also generated predominantly TNB-capped materials.

Figure 5B:
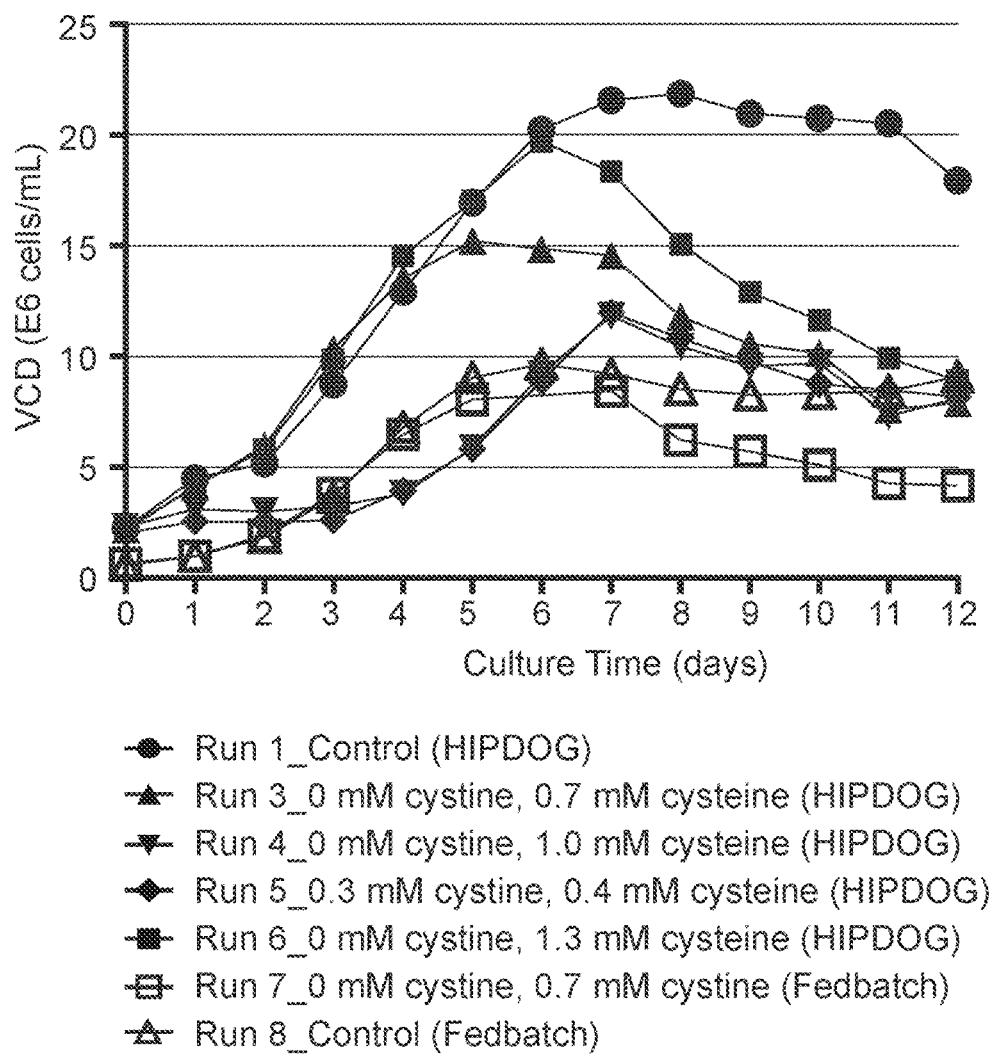
FIG. 5. High cell density culture conditions of stable CHO expression in HiPDOG and fed-batch processes with DTNB. CHO-K1 cells, stably expressing trastuzumab cysteine mutant K183C-K290C, were seeded in proprietary basal medium with the density of 2E6 cells/mL or 0.6E6 cells/mL in a controlled bioreactor. Panel A shows culture conditions of basal media, feed media, or DTNB. Panel B shows viable cell density (VCD).

To further improve TNB-capping efficiency, culture conditions with higher cell density were tested. A glucose-controlled HiPDOG process for better lactate control was utilized (Gagnon et al., Biotechnol Bioeng 2011). Experimental conditions with seed densities and cysteine/cystine media concentrations are shown in FIG. 5A. The lactate controlled HiPDOG process (Run 3) generated a significantly higher peak cell density than the corresponding fed-batch condition (Run 7) (FIG. 5B).

The antibody was purified from the conditioned media and subjected to Cys-capping analysis by LC/MS. As shown in FIG. 6, Fab K183C site achieved more than 95% TNB-capping for condition Runs 3-7, while Fc K290C site had achieved around 98% TNB-capping for condition Runs 3-7.

Figure 7:
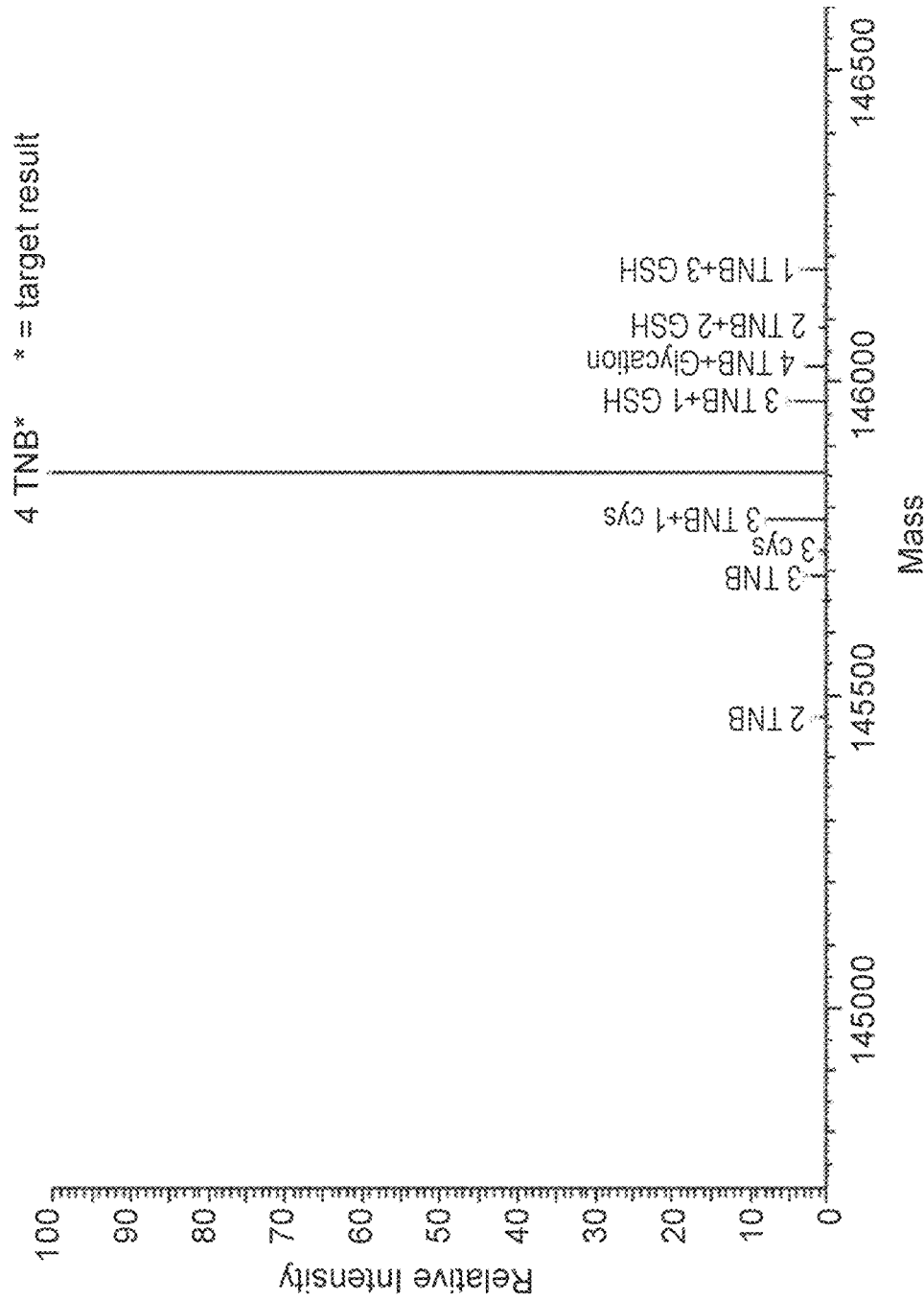
FIG. 7. TNB-capping of generated trastuzumab cysteine mutant K183C-K290C antibodies. Capping was determined by LC/MS analysis, showing the capping species of the mutated cysteine residues. The cysteine mutated antibodies were generated in high cell density culture using proprietary basal and feed media with intentionally depleted cysteine/cystine. A DTNB feed was added to the culture during the production batch. Conditioned media from the culture was ProA purified prior to LC/MS analysis. The primary species produced (>95%) was the desired fully capped mAb with four TNB; low levels of mixed species with less than four TNB caps were present.

Example 3: Generation of Fully TNB-Capped Cysteine Mutant Antibodies in Processes Targeting a Limited Cysteine/Cystine Exposure In the examples below, readouts of capping efficiency for the cysteine mutant antibodies are represented by crude DAR4 (drug to antibody ratio) percentages which are obtained after the conjugation of the linker-payload to the antibody prior to final purification. Crude DAR4 values are being used in these examples as a surrogate marker for capping efficiency; however, determining capping status of each mutated cysteine residue on the antibody can be determined by a lengthier LC/MS analysis (described in Example 1) prior to the conjugation process. An example of the LC/MS analysis can be found in FIG. 7, in which the different capping species per antibody are identified and quantified. The sample used for this analysis was a low cysteine/cystine process with a DTNB feed to produce TNB-capped antibody. The desired target species is four TNB per antibody, which account for >95% in the LC/MS results of this particular example with low levels of non-reducible caps and some sub-4 antibody species.

Example 3.1: Deliberately Limiting Cysteine/Cystine in Culture by Decreasing the Concentration Formulated in the Feed Media Approach 1: This example demonstrates intentionally limiting the cysteine and/or cystine concentrations in the culture, by decreasing the amount of either component formulated in the supplemental feed media. The two conditions used in this example had similar starting concentrations of cysteine and/or cystine in the basal media; however, one condition had no cysteine or cystine components in the nutrient feed medium while the second condition used feed medium which contained cystine only (Table 1); all other process parameters were identical for the two conditions. Standard mammalian cell culture processes incorporate cysteine and/or cystine in additional supplemental feeds due to the solubility challenges of these components in cell culture media.

For this example, CHO-K1 cells stably expressing the cysteine mutant antibody trastuzumab K183C-K290C were used with proprietary basal and feed media in 1 L Applikon bioreactors (Applikon, Inc., Schiedam, Netherlands), operating with BioNet modular controllers (Broadley-James Corp., Irvine, CA) with peristaltic pump and gas mass flow controller modules. The culture was seeded at approximately 2E6 cells/mL, temperature was maintained around 37 degrees Celsius, while pH was controlled near 7.0 by addition of either a sodium/potassium carbonate solution or $CO_2$. Dissolved oxygen levels were controlled >20% of air saturation by sparging of pure oxygen. For TNB-capping of the antibodies, a DTNB feed was started after the growth phase to target a range of 4 mM DTNB concentration in the bioreactor. Batch duration for the examples provided below was approximately 12 days.

The normalized crude DAR4 values demonstrate that the removal of cystine from the feed media proved to be a successful method in depleting the cysteine/cystine available in the culture, which in turn allowed for better capping of the antibody with TNB and a higher percentage of DAR4 antibody-drug conjugates, without detrimental effects on cell growth or productivity.

TABLE 1

Approach 1 - Cysteine and Cystine Media Concentrations and Normalized Crude DAR4 with Trastuzumab K183C-K290C

| Run | Description | Basal Media Cysteine (mM) | Basal Media Cystine (mM) | Nutrient Feed Media Cysteine (mM) | Nutrient Feed Media Cystine (mM) | Peak VCD (E6 cells/mL) | Crude DAR4 (%) |
|---|---|---|---|---|---|---|---|
| 1 | Control | 0.4 | 1.50 | 0 | 4.7 | 47.3 | 1x |
| 2 | No cysteine/cystine in feed | 0.4 | 1.57 | 0 | 0 | 40.4 | 1.24x |

Acquity UPLC (Waters Corp, Milford, MA) was used for amino acid analysis of conditions from a follow-up experiment in which the control condition was dosed with 0.5 mM cystine on days 7, 9, and 11 to avoid cystine limitation at any point in the batch per rational media design as described previously (Table 2); the DTNB target concentration used was 5 mM for TNB-capping. All other process parameters were identical to experiment previously described in Table 1.

TABLE 2

Approach 1 - Cysteine and Cystine Media Concentrations
and Time of Depletion with Trastuzumab K183C-K290C

| | | Basal Media | | Nutrient Feed Media | | Cystine | Cysteine/ Cystine |
|---|---|---|---|---|---|---|---|
| Run | Description | Cysteine (mM) | Cystine (mM) | Cysteine (mM) | Cystine (mM) | Additions (mM) | Depletion (<0.5 mM) |
| 3 | Control | 0.4 | 1.50 | 0 | 4.7 | 0.5 mM on days 7, 9, 11 | n/a |
| 4 | No cysteine/ cystine in feed | 0.4 | 1.57 | 0 | 0 | n/a | Day 6 |

Figure 8:
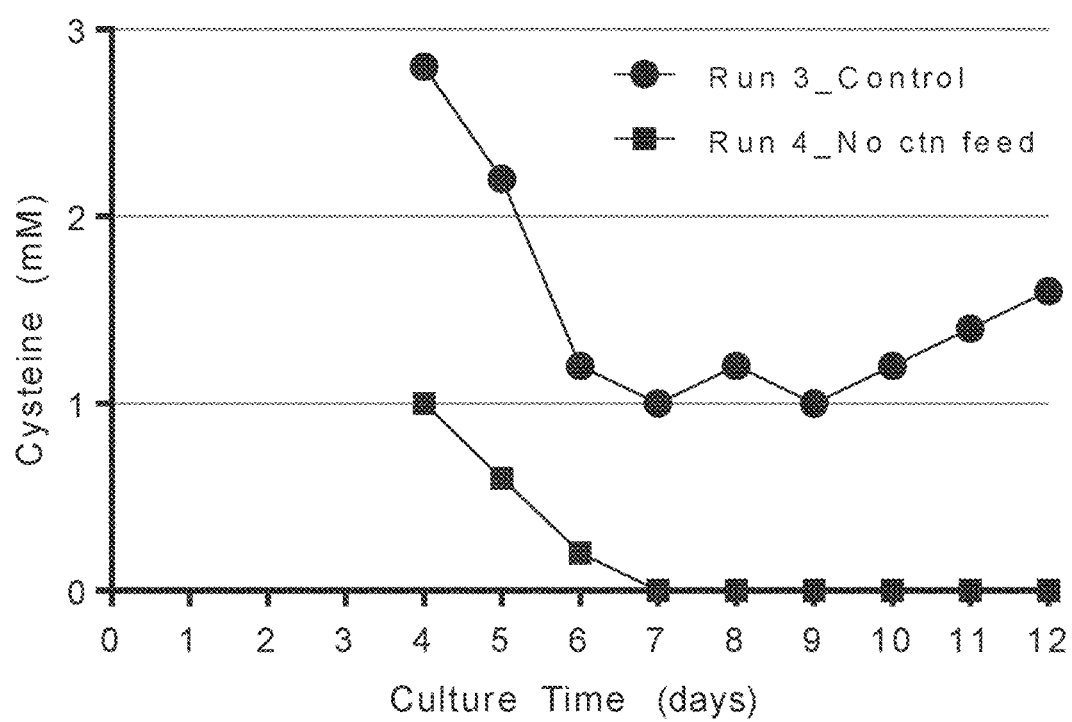
FIG. 8. Cysteine profiles of conditions with high and low cysteine/cystine concentrations in the feed media. Concentrations were obtained by amino acid analysis performed by UPLC; cystine concentrations obtained from UPLC analysis were stoichiometrically converted to cysteine. Both conditions used CHO-K1 cells stably expressing the cysteine mutant antibody trastuzumab K183C-K290C and were run in 1 L bench-scale bioreactors with proprietary basal and feed medium. Both conditions had similar starting concentrations of cysteine/cystine in the basal media, with different concentrations of cystine in the feed media. Conditioned media samples from each condition were analyzed starting on day 4 to obtain a time course of cysteine/cystine depletion throughout the batch.

The results clearly illustrate that removing the cysteine/cystine from the feed media does result in depleted cysteine/cystine concentrations in the culture between days 6-7 for this particular example; cystine concentrations obtained from UPLC analysis were stoichiometrically converted to cysteine and graphically shown in FIG. 8.

It is understood that had the batch duration of this particular example been only through day 5, excess cysteine/cystine would have been available in the culture of Run 4 leading to sub-optimal TNB-capping of the antibody. In this instance, extending the batch duration to day 8 or later was an effective method to deplete excess cysteine/cystine leading to the proper environment for optimal TNB-capping.

Additionally, it is understood that a media exchange strategy, such as perfusion, could be implemented in order to deplete the cysteine/cystine from the culture of Run 4 later in the process. Feed media with higher levels of cysteine/cystine could have been used during the growth phase of the batch and after the peak viable cell density was achieved, a media exchange could have occurred with media containing low levels of cysteine/cystine in order to mimic a very similar profile of cysteine/cystine depletion, comparable to FIG. 8.

Approach 2: This example demonstrates the same strategy presented in Approach 1, of intentionally limiting the cysteine and/or cystine concentrations in the culture by decreasing the amount of either component formulated in the supplemental feed media, but with a second antibody producing cell line. The conditions used in this example were grouped into high or low seed conditions and had similar starting concentrations of cysteine and/or cystine in the basal media. One condition of either high or low seed density had no supplementation of cysteine or cystine aside from the starting concentrations in the basal media, while the remaining conditions had a separate supplemental cystine feed (Table 3); all conditions had a nutrient feed without cysteine or cystine. All other process parameters were identical for the two conditions according to their seed condition (e.g., higher seed density conditions required higher supplemental nutrient feed rate).

For this example, CHO-K1 cells stably expressing the cysteine mutant antibody for anti-EDB K183C-K290C were used with proprietary basal and feed media in 1 L Applikon bioreactors (Applikon, Inc., Schiedam, Netherlands), operating with BioNet modular controllers (Broadley-James Corp., Irvine, CA) with peristaltic pump and gas mass flow controller modules. The culture was seeded at approximately 0.6E6 cells/mL or 3E6 cells/mL, temperature was maintained around 37 degrees Celsius while pH was controlled near 7.0 by addition of either a sodium/potassium carbonate solution or $CO_2$. Dissolved oxygen levels were controlled >20% of air saturation by sparging of pure oxygen. For TNB-capping of the antibodies, a DTNB feed was started after the growth phase to target a range of 4 mM DTNB concentration in the bioreactor. Batch duration for the examples provided below was approximately 12 days.

The evaluation of a second cell line demonstrates that the removal of cysteine and/or cystine from any supplemental feeds is a robust strategy in depleting the cysteine/cystine available in the culture, which then allows for better capping of the antibody with TNB. This strategy ultimately leads to a higher percentage of crude DAR4 antibody-drug conjugates without detrimental effects on cell growth or productivity (Table 3).

TABLE 3

Approach 2 - Cysteine and Cystine Media Concentrations
and Normalized Crude DAR4 with anti-EDB K183C-K290C

| | | | Basal Media | | Supplemental | | Crude |
|---|---|---|---|---|---|---|---|
| Run | Description | High/Low Seed | Cysteine (mM) | Cystine (mM) | Cystine Feed (Day 4 start) | Peak VCD (EG cells/mL) | DAR4 (%) |
| 1 | No cystine feed | High | 0.4 | 1.5 | n/a | 24.8 | 1.2x |
| 2 | +cystine feed | High | 0.4 | 1.5 | 0.25 mM/day | 26.2 | 1x |
| 3 | No cystine feed | Low | 0.4 | 1.1 | n/a | 16.4 | 1.2x |
| 4 | +cystine feed | Low | 0.4 | 1.1 | 0.25 mM/day | 13.9 | 1x |
| 5 | ++cystine feed | Low | 0.4 | 1.1 | 0.50 mM/day | 14.9 | 0.9x |

Figure 9:
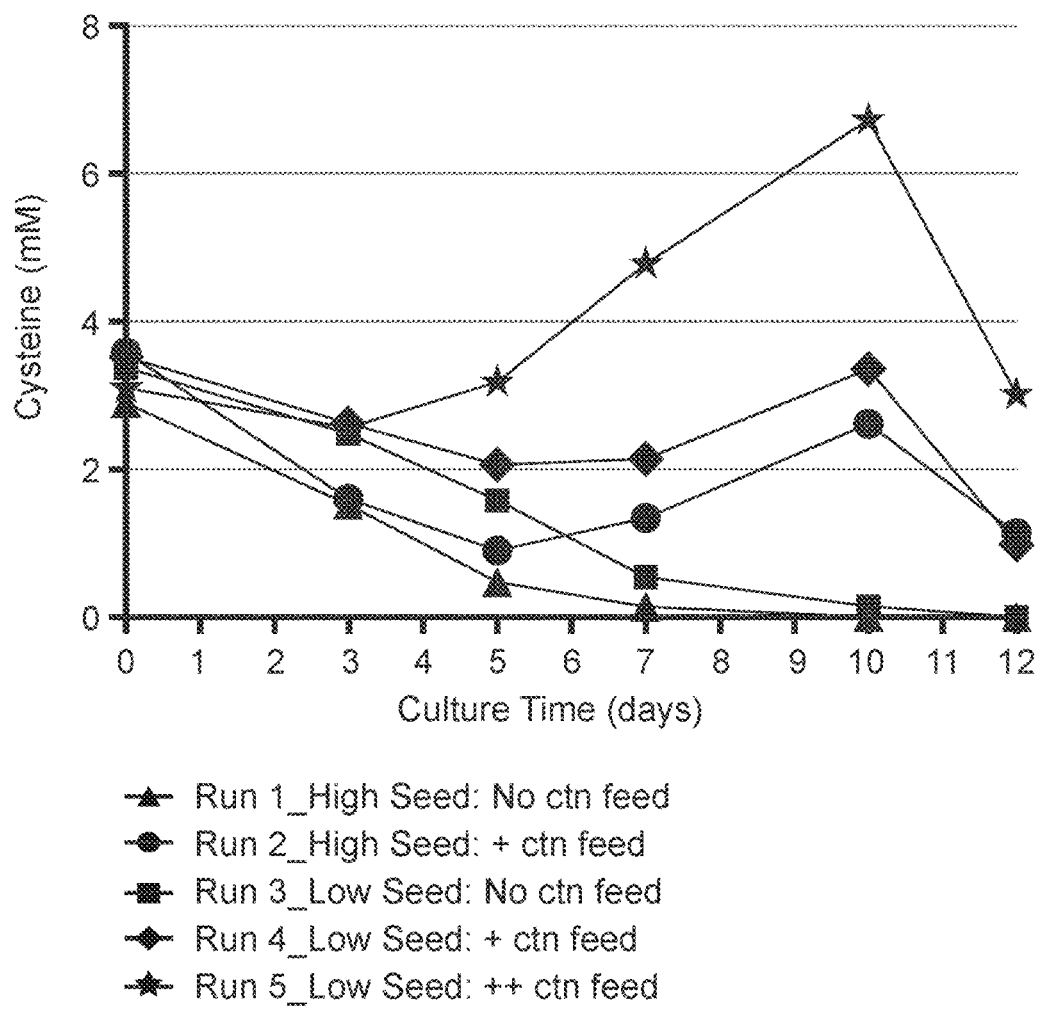
FIG. 9. Cysteine profiles of conditions with high and low supplemental cystine concentrations. Concentrations were obtained by amino acid analysis performed by UPLC; cystine concentrations obtained from UPLC analysis were stoichiometrically converted to cysteine. All conditions used CHO-K1 cells stably expressing the cysteine mutant antibody anti-EDB K183C-K290C and were run in 1 L bench-scale bioreactors with proprietary basal and feed medium. All conditions had similar starting concentrations of cysteine/cystine in the basal media per seed density condition. Conditioned media samples from each condition were analyzed starting on day 0 to obtain a time course of cysteine/cystine depletion throughout the batch.

Acquity UPLC (Waters Corp, Milford, MA) was used for amino acid analysis of the conditions of Approach 2 (Table 4). All cystine concentrations obtained from the UPLC analysis were converted to cysteine and shown in FIG. 9. The results clearly illustrate that removing supplementation of cysteine/cystine does result in depleted concentrations in the culture as early as day 7 (FIG. 9), leading to the proper environment for optimal TNB-capping, as indicated by the crude DAR4 values.

TABLE 4

Approach 2 - Cysteine and Cystine Media Concentrations and Time of Depletion with anti-EDB K183C-K290C

| Run | Description | High/Low Seed | Basal Media Cysteine (mM) | Basal Media Cystine (mM) | Supplemental Cystine Feed (Day 4 start) | Cysteine/Cystine Depletion (<0.5 mM) |
|---|---|---|---|---|---|---|
| 1 | No cystine feed | High | 0.4 | 1.5 | n/a | Day 7 |
| 2 | +cystine feed | High | 0.4 | 1.5 | 0.25 mM/day | n/a |
| 3 | No cystine feed | Low | 0.4 | 1.1 | n/a | Day 8[1] |
| 4 | +cystine feed | Low | 0.4 | 1.1 | 0.25 mM/day | n/a |
| 5 | ++cystine feed | Low | 0.4 | 1.1 | 0.50 mM/day | n/a |

[1] Day 7 value was 0.54 mM; assumed depletion below 0.5 mM by Day 8 based on egrowth performance and productivity of culture

Example 3.2: Limiting Cysteine/Cystine in Culture Using a Stoichiometric Approach and Targeted Fractional Cysteine Limitation Ratios Using rational media design and stoichiometric approaches as described previously, the required amount of cysteine/cystine needed for a particular peak cell density and amount of product produced can be calculated and used to design the optimal media for that specific process (Equation 1). In this example, the required amount of cysteine/cystine was calculated based on rational media design using the estimated peak viable cell density and harvest titer of the process. A range of different fractional cysteine limitation ratios below the calculated required amount of cysteine/cystine (for instance, compared to ratios taught in U.S. Pat. No. 8,232,075 B) were evaluated to find an ideal target ratio that will limit or deplete cysteine/cystine in order to promote TNB-capping of the antibody while still reaching acceptable peak viable cell densities and harvest titers (see Equation 2).

All required cysteine/cystine concentrations were calculated based on the target fractional cysteine limitation ratio and were added to the basal media only.

CHO-K1 cells stably expressing the cysteine mutant antibody trastuzumab K183C-K290C were used with proprietary basal and feed media in 1 L Applikon bioreactors (Applikon, Inc., Schiedam, Netherlands), operating with BioNet modular controllers (Broadley-James Corp., Irvine, CA) with peristaltic pump and gas mass flow controller modules. The culture was seeded at approximately 2E6 cells/mL, temperature was maintained around 37 degrees Celsius, while pH was controlled near 7.0 by addition of either a sodium/potassium carbonate solution or $CO_2$. Dissolved oxygen levels were controlled >20% of air saturation by sparging of pure oxygen. For TNB-capping of the antibody, a DTNB feed was started after the growth phase to target a range of 4 mM DTNB concentration in the bioreactor. Batch duration for the examples provided below was approximately 12 days. Aside from the cysteine/cystine concentrations in the basal media, all process parameters were identical for all of the conditions evaluated.

Table 5 clearly shows that as the fractional cysteine limitation ratio increases, the crude DAR4 percentage (and therefore, capping of the antibody) decreases; this indicates that a lower fractional cysteine limitation ratio is most optimal for capping of the antibody, and in this example ratios of 0.63× and 0.76× provided acceptable peak viable cell densities, harvest titers, and similar capping results (Table 5). Harvest titer and crude DAR4 values have been normalized.

TABLE 5

Fractional Cysteine Limitation Ratio Comparisons

| Run | Actual Fractional Cysteine Limitation Ratio | Peak VCD (E6 cells/mL) | Harvest Titer (g/L) | Crude DAR4 (%) |
|---|---|---|---|---|
| 1 | 0.63× | 32.2 | 1× | 1.40× |
| 2 | 0.76× | 37.0 | 1.1× | 1.35× |
| 3 | 1.15× | 47.0 | 1.8× | 1× |

Figure 10:
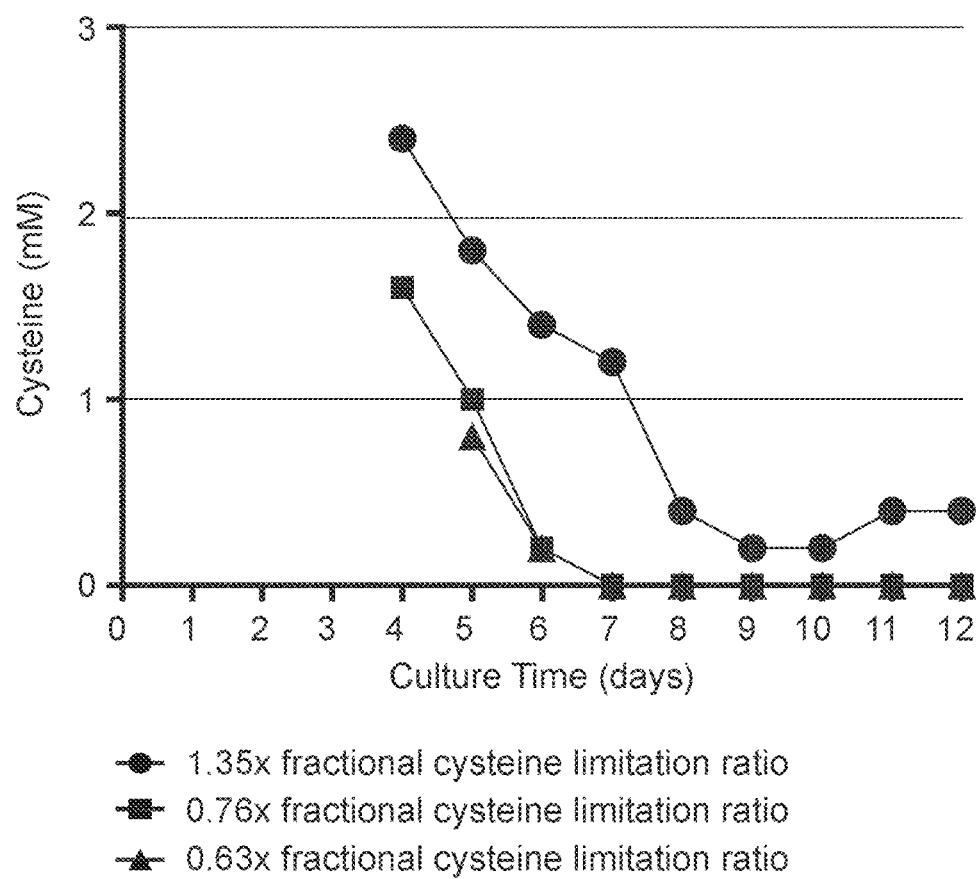
FIG. 10. Cysteine profiles of conditions with target fractional cysteine limitation ratios. Concentrations were obtained by amino acid analysis performed by UPLC; cystine concentrations obtained from UPLC analysis were converted to cysteine. All conditions used CHO-K1 cells stably expressing the cysteine mutant antibody trastuzumab K183C-K290C and were run in 1 L bench-scale bioreactors with proprietary basal and feed medium. The fractional cysteine limitation ratios were determined by using Equations 1 and 2 as previously described; conditions all had different levels of cystine in their respective media to target the desired fractional cysteine limitation ratio. Conditioned media samples from each condition were analyzed starting on day 4 to obtain a time course of cysteine/cystine depletion throughout the batch.

Acquity UPLC (Waters Corp, Milford, MA) was used for amino acid analysis of conditions similar to those described in Table 5.). All cystine concentrations obtained from the UPLC analysis were stoichiometrically converted to cysteine. The results clearly show that lower fractional cysteine limitation ratios lead to depleted levels of cysteine/cystine earlier in the culture as compared to 1.15× condition, indicating that using a target fractional cysteine limitation ratio can lead to a consistent and predictable low level of Cys-capping and high TNB-capping efficiency (FIG. 10).

Example 3.3: Limiting the Cysteine/Cystine in Culture by Increasing the Peak Cell Density As previously demonstrated by two cells lines in Example 3.1, if cysteine/cystine are limited to low concentrations or depleted entirely during the batch, TNB-capping efficiency is increased. A second example of intentionally decreasing or depleting levels cysteine/cystine concentrations in the culture can be done by using peak viable cell density. As the viable cell density increases in a given culture, the consumption of and demand for amino acids typically increases as well (U.S. Pat. No. 8,232,075 B). In this example, two separate conditions were evaluated in which different peak viable cell densities were reached.

CHO-K1 cells stably expressing the cysteine mutant antibody trastuzumab K183C-K290C were used with proprietary basal and feed media in 1 L Applikon bioreactors (Applikon, Inc., Schiedam, Netherlands), operating with BioNet modular controllers (Broadley-James Corp., Irvine, CA) with peristaltic pump and gas mass flow controller modules. Conditions were seeded at approximately 0.6E6 or 2E6 cells/mL, temperature was maintained around 37 degrees Celsius, while pH was controlled near 7.0 by addition of either a sodium/potassium carbonate solution or $CO_2$. Dissolved oxygen levels were controlled >20% of air saturation by sparging of pure oxygen. Batch duration for the examples provided below was approximately 12 days; one condition was harvested early due to low viability. Some process parameters, such as nutrient feed rates, for the two conditions differed in order to reach and sustain different peak cell densities. However, the cysteine and cystine concentrations in the basal media were similar and the feed media cystine concentrations were the same (Table 6).

TABLE 6

Cysteine and Cystine Media Concentrations

| Run | Description | Basal Media | | Nutrient Feed Media | | Feed Rate | Peak VCD (E6 cells/mL) |
| --- | --- | --- | --- | --- | --- | --- | --- |
| | | Cystine (mM) | Cysteine (mM) | Cystine (mM) | Cysteine (mM) | | |
| 1 | Low Seed | 1.10 | 0.4 | 4.7 | 0 | 1x | 15.2 |
| 2 | High Seed | 1.50 | 0.4 | 4.7 | 0 | 3.4x | 40.0 |

Figure 11A:
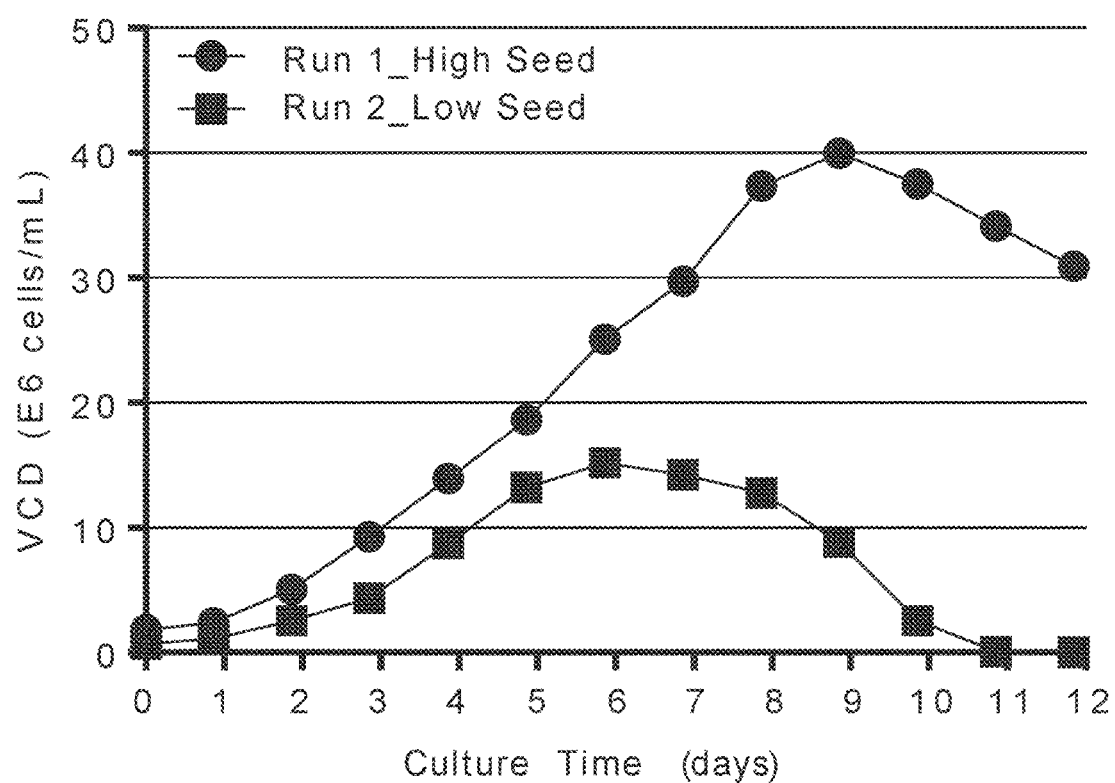
FIG. 11. Viable cell density and cysteine concentration profiles of high and low peak cell density conditions. High and low peak cell densities were achieved with CHO-K1 cells stably expressing the cysteine mutant antibody trastuzumab K183C-K290C. Both conditions were run 1 L bench-scale bioreactors with proprietary basal and feed medium; although some process parameters differed for the two conditions in order to reach and maintain different peak densities, the cysteine/cystine concentrations were similar in the basal media and identical in the feed media. Panel A shows the viable cell density. Panel B shows the cysteine concentrations during the batch. Conditioned media samples from each condition were analyzed starting on day 0 to obtain a time course of cysteine/cystine depletion throughout the batch. Amino acid analysis was performed by UPLC; cystine concentrations obtained from UPLC analysis were stoichiometrically converted to cysteine FIG. 12. Crude DAR4 results of DTNB addition to condition media. CHO-K1 cells stably expressing the cysteine mutant antibody trastuzumab K183C-K290C were cultivated in 1 L bioreactors using proprietary basal and feed media. After cultivation in the bioreactor reached a particular time point in the batch duration, the cells were separated from the conditioned medium by centrifugation and 0.2 μm filtration. The conditioned medium was transferred to a separate vessel and dosed with 2 mM DTNB and incubated for various lengths of time. Samples of the different incubation times were ProA purified and conjugated using the TNB conjugation base process (see Example 5), determining the crude DAR4 percentage which is used as a surrogate marker of fully TNB-capped antibodies.
Figure 11B:
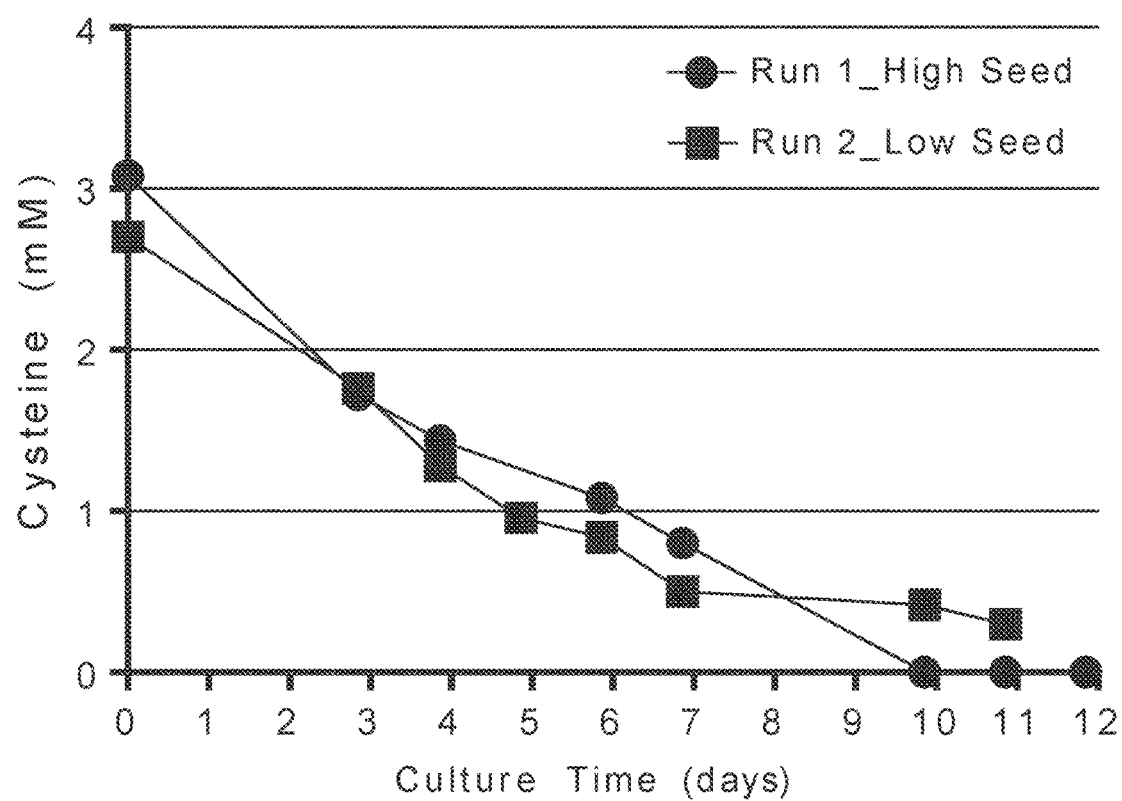

Acquity UPLC (Waters Corp, Milford, MA) was used for amino acid analysis of conditions described in Table 6. All cystine concentrations obtained from the UPLC analysis were converted to cysteine. Amino acid analysis of these conditions showed that the condition with the higher peak viable cell density successfully depleted cysteine/cystine earlier in the batch, as compared to the condition with the lower peak viable cell density (FIG. 11B) which maintained a residual concentration of cysteine/cystine until harvest. Crude DAR4 was not analyzed for these samples but based on the amino acid analysis data; cysteine/cystine was depleted earlier for the high seed condition. From this data it can be inferred that an optimal low cysteine/cystine environment for efficient TNB-capping was induced by the higher peak viable cell density. This demonstrates that fostering conditions that can promote cultures to reach higher cell densities can be an effective alternative method in keeping cysteine/cystine at low or depleted levels in the cell culture to promote a desirable environment for TNB-capping of the antibody.

Example 4. Generation of TNB-Capped Cys Mutant Antibody in the Absence of Cells

The generation of an antibody or a fusion protein in a form so that it may be subsequently used in a conjugation step to generate a desired antibody drug conjugate is routinely achieved as part of the development of a manufacturing cell line and/or achieved as part of the upstream/cell culture process portion of a manufacturing process. In the case of generation of TNB-capped antibody, the approach thus far described has been through inclusion of a DTNB feed as part of the cell culture process along with or without various additional modifications of the cell culture process (such as, but not limited to, adjustments of cysteine/cystine feed concentrations, batch length modifications) as previous described. While this enables production of the desired capped antibody, these approaches depend upon the cell culture portion of the manufacturing process, and can reduce overall productivity of the manufacturing facility. Thus, throughput of the TNB-capped antibody is limited because of suboptimal utilization of the facility, specifically of the production bioreactor or fermenter used for cell culture.

In this example, a cysteine mutant recombinant protein, such as a cysteine mutant antibody, a cysteine mutant fusion protein, or the like, is produced via cell culture/fermentation techniques. The protein containing conditioned medium may then be separated from cells by centrifugation, microfiltration or other suitable cell separation technique. Cell separation may be complete or partial. The next step is the exposure/incubation of the mutant cys recombinant protein with DTNB to generate TNB-capped protein. By separating the steps of a) generating cysteine mutant recombinant protein and b) capping of cysteine mutant recombinant protein, manufacturing process and facility may be optimized to maximize productivity by avoiding utilizing the cell culture bioreactor/fermenter in the capping portion of the process and thus minimizing the cycle time required of the bioreactor/fermenter. Minimizing the cycle time of the bioreactor/fermenter thus allows for higher throughput (via higher number of cycles executed per period of time).

Figure 12:
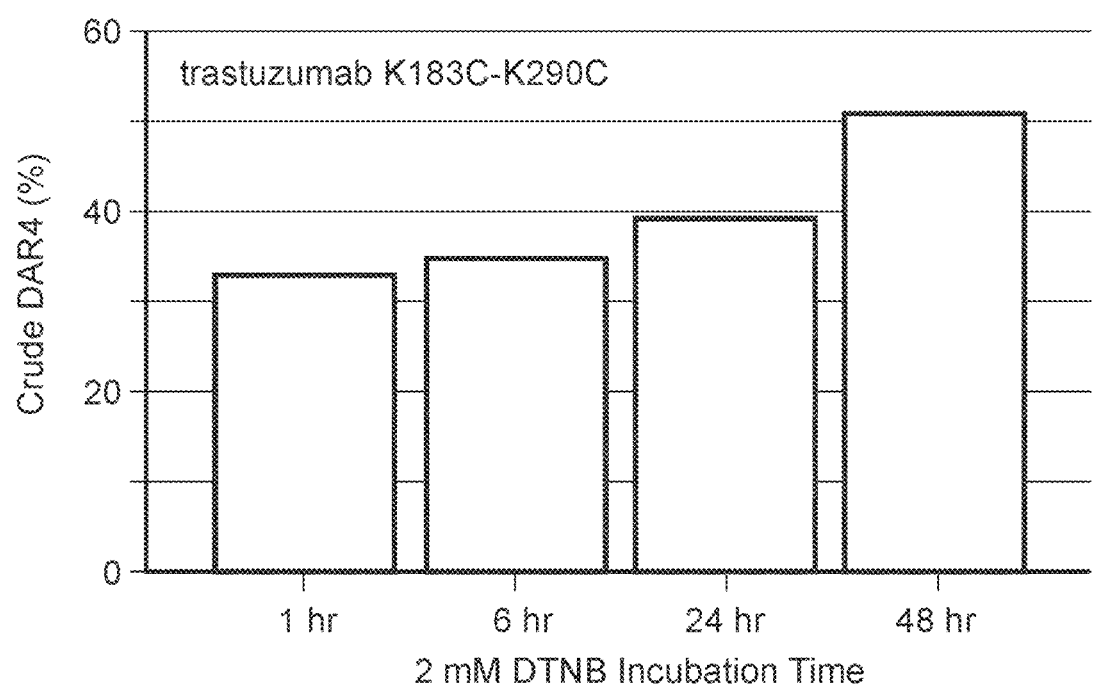

Approach 1: For this example, CHO-K1 cells stably expressing the cysteine mutant antibody trastuzumab K183C-K290C were used with basal and feed media in 1 L Applikon bioreactors (Applikon, Inc., Schiedam, Netherlands), operating with BioNet modular controllers (Broadley-James Corp., Irvine, CA) with peristaltic pump and gas mass flow controller modules. The cell culture temperature was maintained around 37 degrees Celsius, while pH was controlled near 7.0 by addition of either a sodium/potassium carbonate solution or $CO_2$. Dissolved oxygen levels were controlled >20% of air saturation by sparging of pure oxygen. After cell culture cultivation, the protein containing conditioned medium was separated via centrifugation and 0.2 um filtration. The conditioned medium was then transferred to a separate vessel. To this vessel, a particular concentration of DTNB was directly added to the protein containing conditioned medium. The reaction was allowed to occur for a various periods of time so as to demonstrate the robustness of the procedure to generate the desired material. As can be seen in FIG. 12 (trastuzumab K183C-K290C), desired product was generated using a range of incubation periods, with longer times leading to improved performance.

Figure 13:
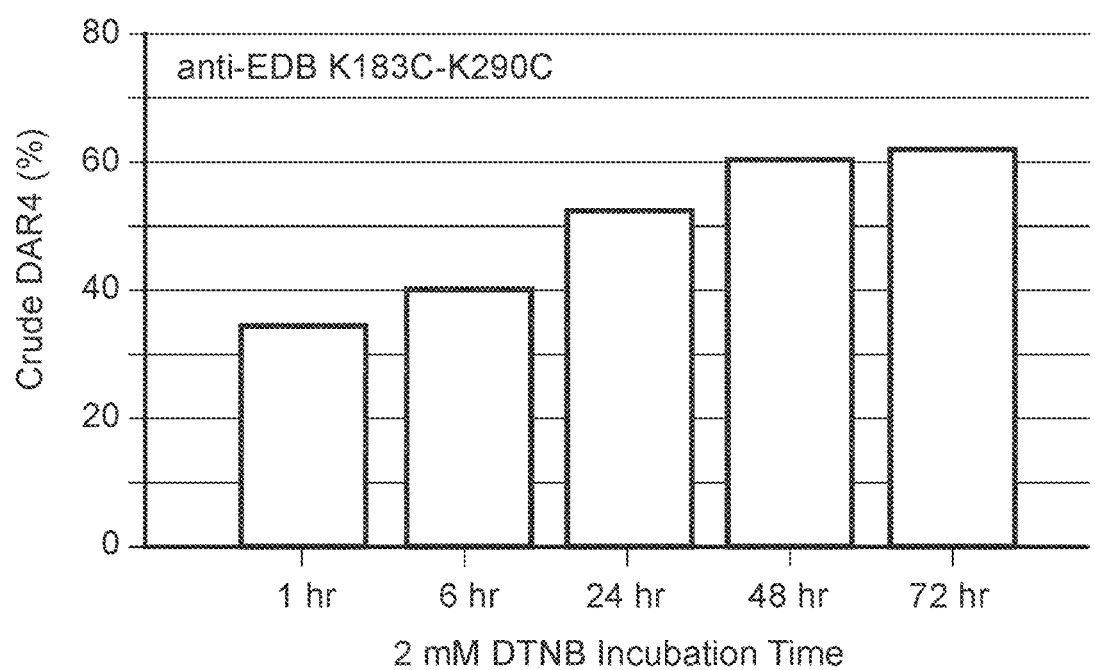
FIG. 13. Crude DAR4 results of DTNB addition to condition media. CHO-K1 cells stably expressing the cysteine mutant antibody anti-EDB K183C-K290C were cultivated in 1 L bioreactors using proprietary basal and feed media. After cultivation in the bioreactor reached a particular time point in the batch duration, the cells were separated from the conditioned medium by centrifugation and 0.2 μm filtration. The conditioned medium was transferred to a separate vessel and dosed with 2 mM DTNB and incubated for various lengths of time. Samples of the different incubation times were ProA purified and conjugated using the TNB conjugation base process (see Example 5), determining the crude DAR4 percentage which is used as a surrogate marker of fully TNB-capped antibodies.

Approach 2: For this example, a second cell line of CHO-K1 cells stably expressing the cysteine mutant antibody anti-EDB K183C-K290C were used with basal and feed media in 1 L Applikon bioreactors (Applikon, Inc., Schiedam, Netherlands), operating with BioNet modular controllers (Broadley-James Corp., Irvine, CA) with pump and gas mass flow controller modules. The cell culture temperature was maintained around 37 degrees Celsius, while pH was controlled near 7.0 by either a sodium/potassium carbonate solution or $CO_2$. Dissolved oxygen levels were controlled >20% of air saturation by sparging of pure oxygen. After cell culture cultivation, the protein containing conditioned medium was separated centrifugation and 0.2 um filtration. The conditioned medium was then transferred to a separate vessel. To this vessel, a particular concentration of DTNB was directly added to the protein containing conditioned medium. The reaction was allowed to occur for a various periods of time so as to demonstrate the robustness of the procedure to generate the desired material. As can be seen in FIG. 13 (anti-EDB K183C-K290C), desired product was generated using a range of incubation periods, with longer times leading to improved performance demonstrating the same trend observed in two different antibody expressing cell lines

Example 5: TNB Conjugation Process

Cysteine mutant antibody capped with TNB is selectively reduced with TSPP. Free thiol groups generated allow direct drug conjugation without the ultrafiltration/diafiltration (UF/DF) and reoxidation steps, which simplifies the process. Cysteine mutant antibody trastuzumab K183C-K290C fully capped with TNB in the form of 4 cappings per antibody (DAR4) was generated and direct-conjugated after TSPP treatment with an efficiency of 70%.

As a further example, TNB-capping and conjugation (at K183C-K290C) is herein discussed. The TNB-capped conjugation protocol for cysteine mutant conjugation consists of two steps leading to the crude conjugate: selective reduction and conjugation. In the first step a selective reduction of mutant cysteines is accomplished to achieve the removal of protecting group(s) from mutant cysteine residues with minimal or no reduction of interchain disulfides. Typically this is done using an excess (~7 equivalents) of a reducing agent such as tris(3-sulfonatophenyl)phosphine (TSPP) at ambient temperature for 2 h. In a second step the unprotected mutant cysteines are conjugated to linker-payload. Typically an excess (~12 equivalents) of linker-payload is added to reaction and the reaction is done at ambient temperature for 1 h to produce the crude conjugate. The final conjugate maintains the native interchain disulfide bonds, since they were not broken during the reduction step.

In a specific instance: To 1.0 g (6.9 µmol; 25 mg/mL in 60 mM histidine, pH 7; 38.9 mL) of trastuzumab K183C-K290C antibody was added 27.5 mg of TSPP (7 equivalents; 48.3 µmol; 10 mM in water; 4.83 mL). The reaction mixture was incubated at ambient temperature for 2 h. To this reaction mixture was added 111 mg of mcvcPABC0101 linker-payload (12 equivalents, 82.7 µmol; 25 mM in dimethylsulfoxide; 3.31 mL). The reaction mixture was incubated at ambient temperature for 1 h to afford crude conjugate.

Example 6: TNB Conjugation Process with Post-Reduction Diafiltration

Figure 14:
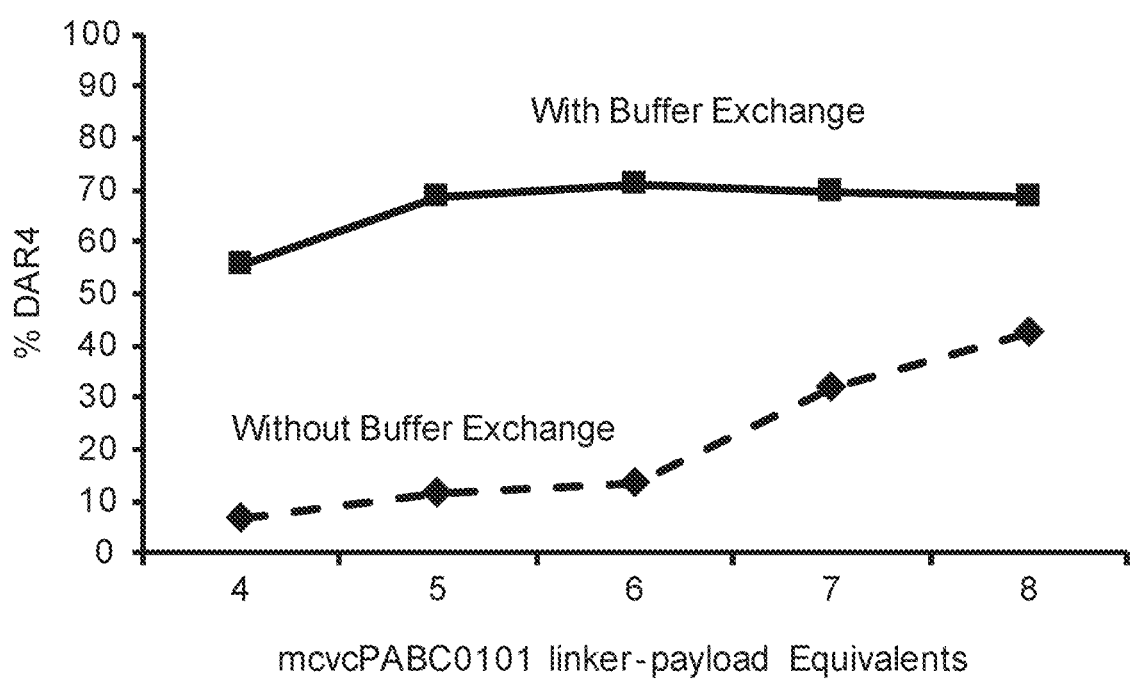
FIG. 14. Impact of post-reduction buffer exchange. TNB-capped trastuzumab K183C-K290C antibody was reduced with 6 equivalents of TSPP (37° C. for 3 h) and conjugated with varying amounts of mcvcPABC0101; squares: buffer exchange after reduction, diamonds: no buffer exchange. % DAR4 was measured by analytical hydrophobic interaction chromatography.

The amount of excess linker-payload used in the process described in Example 5 can be reduced by adding a diafiltration (buffer exchange) step after the TSPP reduction to remove species that react with linker-payload. As shown in FIG. 14, 70% DAR4 is achieved with 6 equivalents of linker payload following buffer exchange, while significantly higher equivalents are needed when buffer exchange is not performed. Also, the amount of TSPP can be slightly reduced by increasing reduction temperature and/or time.

In a specific instance: To 4.0 g (27.6 µmol; 25 mg/mL in 60 mM histidine, pH 7; 156 mL) of trastuzumab K183C-K290C antibody was added 93.8 mg of TSPP (6 equivalents; 165 µmol; 10 mM in water; 16.5 mL). The reaction mixture was incubated at 37° C. for 3 h, and then buffer exchanged by diafiltration (TangenX ProStream 50 kD membrane, 110-210 g/m$^2$, 10 diavolumes of 60 mM histidine, pH 7). Following diafiltration, 222 mg of mcvcPABC0101 linker-payload (6 equivalents, 165 µmol; 25 mM in dimethylsulfoxide; 6.62 mL) was added. The reaction mixture was incubated at 25° C. for 1 h to afford crude conjugate.

Figure 15:
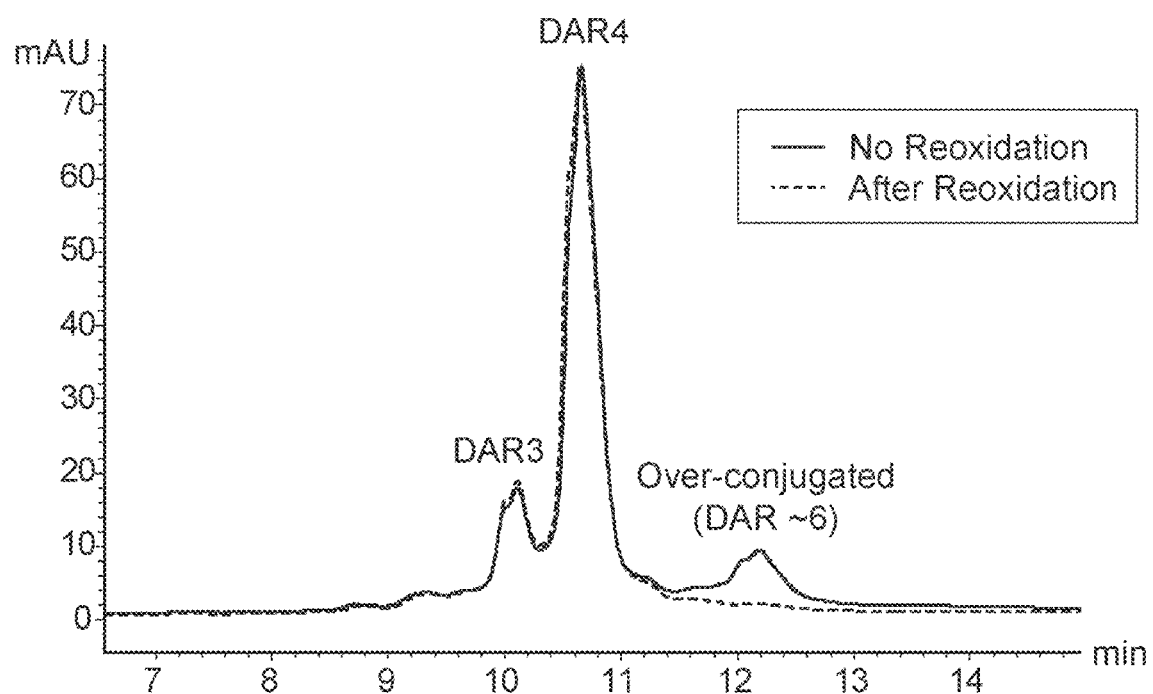
FIG. 15. Impact of reoxidation step. Analytcal hydrophobic interaction chromatography traces (detection at 280 nm) following reduction with 20 equivalents of TSPP, buffer exchange, and conjugation with 10 equivalents of mcvcPABC0101; black trace: no reoxidation, gray trace: reoxidation with dehydroascorbic acid prior to conjugation. Over-conjugated species result from conjugation to reduced interchain disulfide bonds.

Example 7: TNB Conjugation Process with Increased TSPP Stoichiometry, Post-Reduction Diafiltration, and Reoxidation The amount of aggregate produced by the process described in Example 6 can be reduced by increasing the TSPP stoichiometry. An increased TSPP stoichiometry more rapidly removes the TNB from mutated cysteines and prevents the formation of disulfide bonds between antibodies. However, increased TSPP stoichiometry also results in reduction of a small fraction of interchain disulfide bonds. The presence of sodium chloride and other salts (see Example 8) decreases the extent of interchain disulfide reduction at higher TSPP stoichiometry. Addition of a reoxidation step following diafiltration repairs some of the reduced interchain disulfide bonds. As shown in FIG. 15, conjugation following reduction with 20 equivalents of TSPP and buffer exchange, with no reoxidation step, results in low levels of over-conjugated species due to interchain disulfide bond reduction. When reoxidation is added to the process, over-conjugated species are not formed.

In a specific instance: To 24.7 g (0.170 mmol; 26 mg/mL in 60 mM histidine, 150 mM NaCl, pH 7; 961 mL) of trastuzumab K183C-K290C antibody was added 1.94 g of TSPP (20 equivalents; 3.41 mmol; 100 mM in water; 34.1 mL). The reaction mixture was agitated at 37° C. for 3 h, and then buffer exchanged by diafiltration (TangenX ProStream 50 kD membrane, 110-210 g/m$^2$, 10 diavolumes of 60 mM histidine, 150 mM NaCl, pH 7). Following diafiltration, the mixture was cooled to 4° C., 0.45 g dehydroascorbic acid (15 equivalents; 2.56 mmol; 50 mM in 1:1 DMSO/water; 51.2 mL) was added, and the mixture was agitated at 4° C. for 16 h. The mixture was heated to 25° C., 1.37 g of mcvcPABC0101 linker-payload (6 quivalents, 1.02 mmol; 25 mM in dimethylsulfoxide; 40.9 mL) was added, and the mixture was agitated at 25° C. for 1.5 h to afford crude conjugate.

Example 8: TNB Conjugation Process with Increased TSPP Stoichiometry, Post-Reduction Diafiltration, Reoxidation, and Linker-Payload Quench The presence of salts in the reduction mixture, such as sodium chloride in Example 7, decreases the extent of interchain disulfide reduction at higher TSPP stoichiometry. As a further example, using the measure from FIG. 15 of over-conjugated species formed when no reoxidation is performed, interchain disulfide reduction decreased from ~33% when no salt was present to 10-20% in the presence of 150-500 mM salts. Salts such as sodium chloride, sodium acetate, potassium nitrate, potassium hydrogen phosphate, magnesium nitrate, magnesium sulfate, guanidinium chloride, and ammonium sulfate decreased interchain disulfide reduction.

In a specific instance, interchain disulfide reduction was decreased from 33% when no salt was added to 15%, 14%, and 12% in the presence of 150 mM, 250 mM, and 500 mM sodium chloride, respectively.

Example 9: TNB Conjugation Process with Increased TSPP Stoichiometry, Post-Reduction Diafiltration, Reoxidation, and Linker-Payload Quench This example is similar to Example 7, but features (1) reoxidation run at 25° C., which significantly reduces reoxidation time and eliminates time-consuming cooling after diafiltration and heating prior to conjugation, and (2) quenching of linker-payload by reaction with cysteine, which improves downstream purification under certain conditions (see Example 14 below).

In a specific instance: To 80.0 g (0.541 mmol; 26 mg/mL in 60 mM histidine, 150 mM NaCl, pH 7; 3053 mL) of trastuzumab K183C-K290C antibody was added 6.14 g of TSPP (20 equivalents; 10.8 mmol; 100 mM in water; 108 mL). The reaction mixture was agitated at 37° C. for 3 h, and then buffer exchanged by diafiltration (TangenX ProStream 50 kD membrane, 110-210 g/m$^2$, 10 diavolumes of 60 mM histidine, 150 mM NaCl, pH 7). Following diafiltration, 0.19 g dehydroascorbic acid (2 equivalents; 1.08 mmol; 50 mM in 1:1 DMSO/water; 21.6 mL) was added, and the mixture was agitated at 25° C. for 0.5 h. Then, 4.35 g of mcvcPABC0101 linker-payload (6 quivalents, 3.24 mmol; 25 mM in dimethylsulfoxide; 130 mL) was added, and the mixture was agitated at 25° C. for 1 h. Lastly, 0.79 g cysteine (12 quivalents, 6.48 mmol; 100 mM in water; 64.9 mL) was added, and the mixture was agitated at 25° C. for 1 h to afford crude conjugate.

Example 10: TNB Conjugation Process—Antibody Fragment Repair by Reoxidation

The addition of a reoxidation step, as in Examples 7 and 9, repaired fragments present in the incoming antibody, thus improving the quality and yield of the final conjugate. Fragments originate from antibodies in which one or more of the interchain disulfide bonds is not intact. Thus, conjugation of antibody lots containing fragment levels of 15-35% using the process described in Example 9 produced conjugate with low and comparable levels of fragments.

In a specific instance: Antibody with 35% fragments produced crude conjugate with approximately 10% fragments; the majority of fragments were repaired by the reoxidation. The final purified conjugate contained less than 3% fragments.

Example 11: TNB Conjugation Process with Anti-EDB K183C-K290C Antibody

The TNB conjugation process is suitable for TNB-capped antibodies other than trastuzumab.

Figure 16:
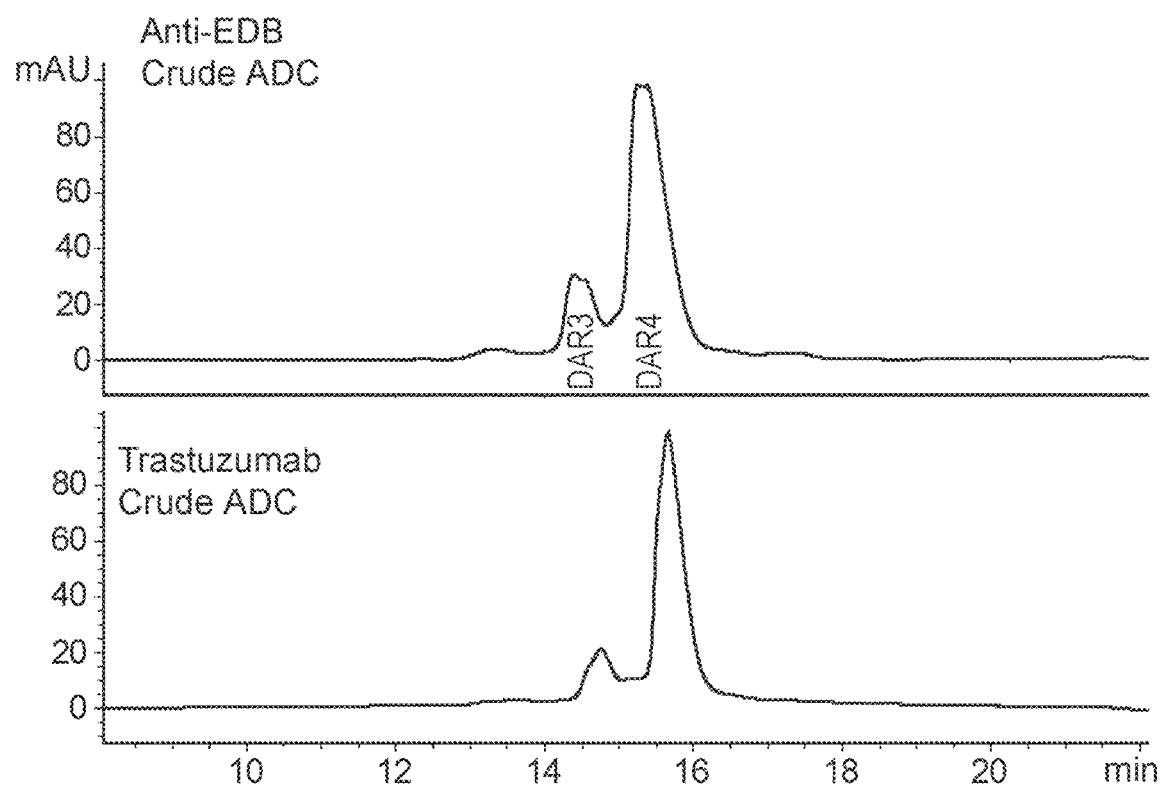
FIG. 16. Comparison of crude conjugates of cysteine mutant anti-EDB antibody K183C-K290C and cysteine mutant antibody trastuzumab K183C-K290C. Conjugates were generated following the protocol described below in Example 9 and analyzed by analytical hydrophobic interaction chromatography (detection at 280 nm).

In a specific instance: Processing of anti-EDB K183C-K290C antibody capped with TNB using the procedure described in Example 9 afforded crude conjugate comparable to that obtained with trastuzumab K183C-K290C antibody. As shown in FIG. 16, the crude conjugates of these antibodies are highly similar with ~75% DAR4.

Example 12: Purification of Conjugates Produced by the TNB Conjugation Process

Crude conjugate produced by the process can be purified by hydrophobic interaction chromatography (HIC). HIC purification removes or significantly reduces free linker-payload, aggregates, fragments, and lower-DAR conjugates. As a further example, HIC purification can be accomplished using a Capto™ Butyl ImpRes resin (GE) column and a Toyopearl® PPG-600M (Tosoh) column connected in series. Capto™ Butyl ImpRes provides suitable removal of aggregates, fragments, and lower-DAR conjugates, and Toyopearl® PPG-600M retains free mcvcPABC0101 linker-payload. Purified conjugate can be concentrated and buffer exchanged by ultrafiltration/diafiltration (UF/DF). UF/DF also can remove residual free linker-payload if present after HIC purification.

In a specific instance: Crude conjugate (4.0 g, 26 mg/mL) produced by the process described in Example 6 was diluted with one volume of 10 mM sodium phosphate, pH 7. The diluted crude mixture was further diluted 1:1 with 20 mM sodium phosphate, 1M ammonium sulfate, pH 7, to afford the HIC loading solution. HIC purification was accomplished using a Capto™ Butyl ImpRes resin (GE) column (24 cm (h)×2.6 cm (d)) and a Toyopearl® PPG-600M (Tosoh) column ((4 cm (h)×2.6 cm (d)) connected in series. Following introduction of the loading solution onto the Capto™ Butyl ImpRes column, the purified conjugate was eluted from the two-column series with a gradient of 50-100% buffer B in buffer A over 25 column volumes; buffer A: 20 mM sodium phosphate, 1 M ammonium sulfate, pH 7; buffer B: 10 mM sodium phosphate, pH 7. Fractions containing desired conjugate were pooled and subjected to UF/DF for concentration and buffer exchange (TangenX ProStream 50 kD membrane, 110-210 g/m$^2$, 10 diavolumes of 20 mM histidine, pH 5.8).

Example 13: Purification of Conjugates Produced by the TNB Conjugation Process with Increased Recovery When purifying by HIC, recovery of DAR4 ADC can be improved by addition of isopropanol to mobile phase buffer B, thus increasing process yield.

In a specific instance: Crude conjugate (12.4 g, 26 mg/mL) produced by the process described in Example 7 was diluted with one volume of 10 mM sodium phosphate, pH 7, 5% (v/v) isopropanol. The diluted crude mixture was further diluted 1:1 with 20 mM sodium phosphate, 1M ammonium sulfate, pH 7, to afford the HIC loading solution. HIC purification was accomplished using a Capto™ Butyl ImpRes resin (GE) column (22 cm (h)×5 cm (d)) and a Toyopearl® PPG-600M (Tosoh) column ((4 cm (h)×5 cm (d)) connected in series. Following introduction of the loading solution onto the Capto™ Butyl ImpRes column, the purified conjugate was eluted from the two-column series with a gradient of 50-100% buffer B in buffer A over 25 column volumes; buffer A: 20 mM sodium phosphate, 1M ammonium sulfate, pH 7; buffer B: 10 mM sodium phosphate, pH 7, 5% (v/v) isopropanol. Fractions containing desired conjugate were pooled and subjected to UF/DF for concentration and buffer exchange (TangenX ProStream 50 kD membrane, 110-210 g/m$^2$, 10 diavolumes of 20 mM histidine, pH 5.8). The ADC yield for the overall process, where isopropanol was present in buffer B in the HIC purification, was improved by approximately 50% over that which used the purification process in Example 12.

Figure 17:
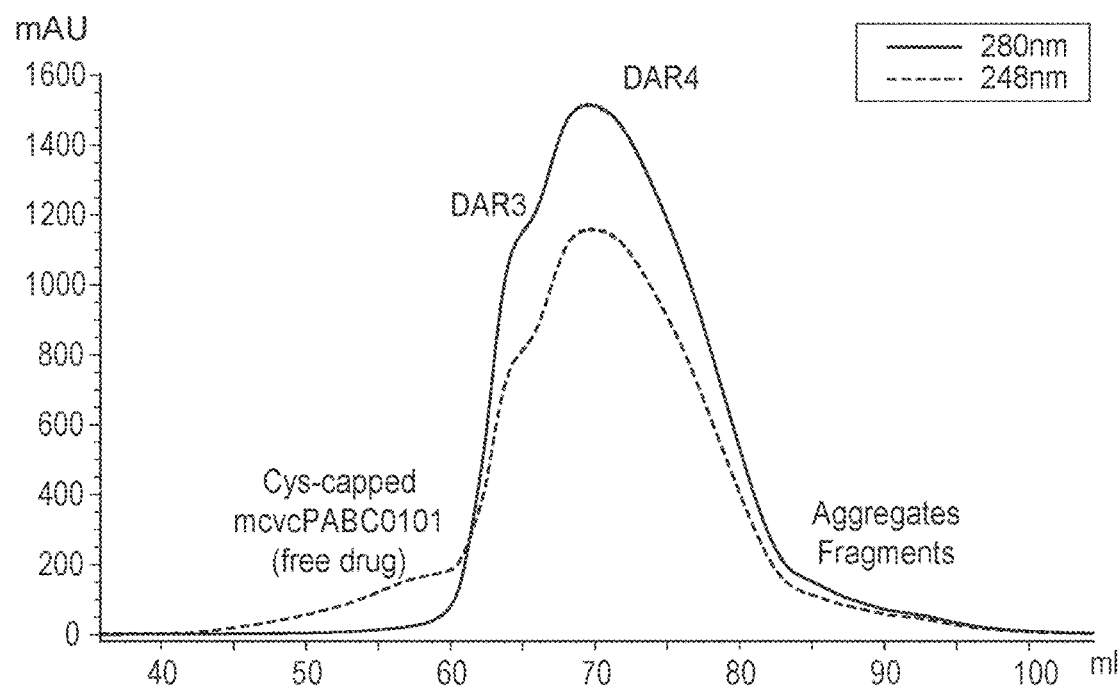
FIG. 17. Hydrophobic interaction chromatography purification of a cysteine mutant trastuzumab conjugate. Crude conjugate prepared following the procedure described in Example 9 and purified using the column and conditions described in Example 14.
Figure 18:
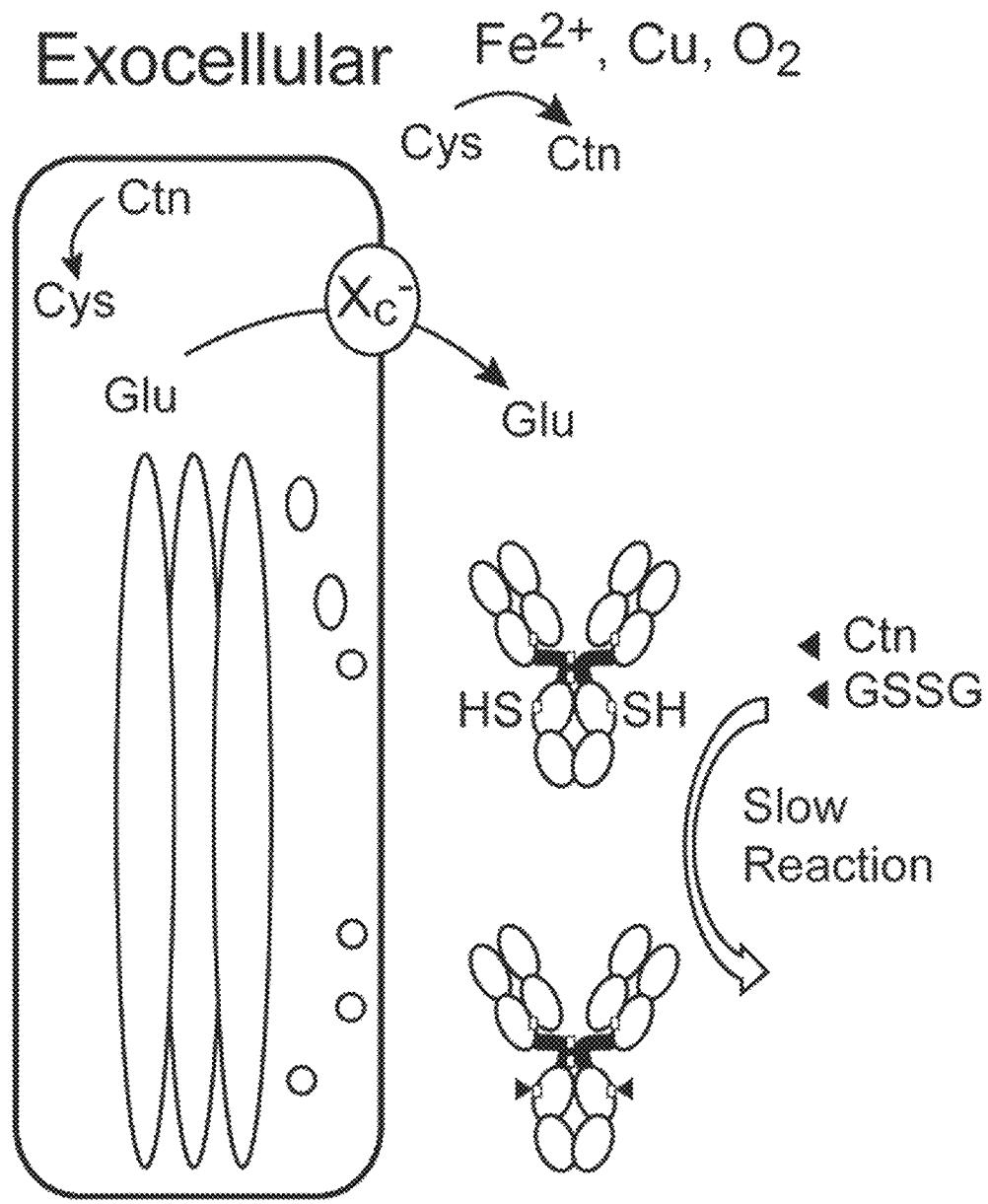
FIG. 18. A schematic representation of an example of cysteine utilization during cell culture.

Example 14: Purification of Conjugates Produced by the TNB Conjugation Process with Linker-Payload Quench When the mcvcPABC0101 linker-payload is capped with cysteine in a quench step, as in Example 9, HIC purification can be accomplished using a Capto™ Butyl ImpRes resin (GE) column alone. Cysteine-capped mcvcPABC0101 elutes earlier than DAR4 conjugate and is well-separated on a Capto™ Butyl ImpRes column. As shown in FIG. 17, DAR4 conjugate is separated from cysteine-capped mcvcPABC0101, lower-DAR conjugates, aggregates, and fragments using conditions described in this example. Cysteine-capped mcvcPABC0101 is also easily cleared by diafiltration.

In a specific instance: Crude conjugate (40.0 g, 26 mg/mL) produced by the process described in Example 9 was diluted with one volume of 10 mM sodium phosphate, pH 7, 5% (v/v) isopropanol. The diluted crude mixture was further diluted 1:1 with 20 mM sodium phosphate, 1M ammonium sulfate, pH 7, to afford the HIC loading solution. HIC purification was accomplished using a Capto™ Butyl ImpRes resin (GE) column (24.5 cm (h)×10 cm (d)). Following introduction of the loading solution onto the column, the purified conjugate was eluted with a gradient of 50-100% buffer B in buffer A over 10 column volumes; buffer A: 20 mM sodium phosphate, 1M ammonium sulfate, pH 7; buffer B: 10 mM sodium phosphate, pH 7, 5% (v/v) isopropanol. Fractions containing desired conjugate were pooled and subjected to UF/DF for concentration and buffer exchange (TangenX ProStream 50 kD membrane, 110-210 g/m$^2$, 10 diavolumes of 20 mM histidine, pH 5.8).

In a separate specific instance: Crude conjugate (0.83 g, ~23 mg/mL) produced by the process described in Example 9 was diluted with one volume of 10 mM sodium phosphate, pH 7, 5% (v/v) isopropanol. The diluted crude mixture was further diluted 1:1 with 20 mM sodium phosphate, 1M ammonium sulfate, pH 7, to afford the HIC loading solution. HIC purification was accomplished using a Butyl HP resin (GE) column (24 cm (h)×1.6 cm (d)) and a Toyopearl® PPG-600M (Tosoh) column ((5.3 cm (h)×1.6 cm (d)) connected in series. Following introduction of the loading solution onto the column, the purified conjugate was eluted with a gradient of 50-100% buffer B in buffer A over 10 column volumes; buffer A: 20 mM sodium phosphate, 1M ammonium sulfate, pH 7; buffer B: 10 mM sodium phosphate, pH 7, 5% (v/v) isopropanol. Fractions containing desired conjugate were pooled. High recovery was achieved along with separation of mcvcPABC0101 linker-payload from the DAR4 conjugate.

Example 15: Assay to Analyze Disulfide Scrambling at Hinge Region of Antibody

Figure 20:
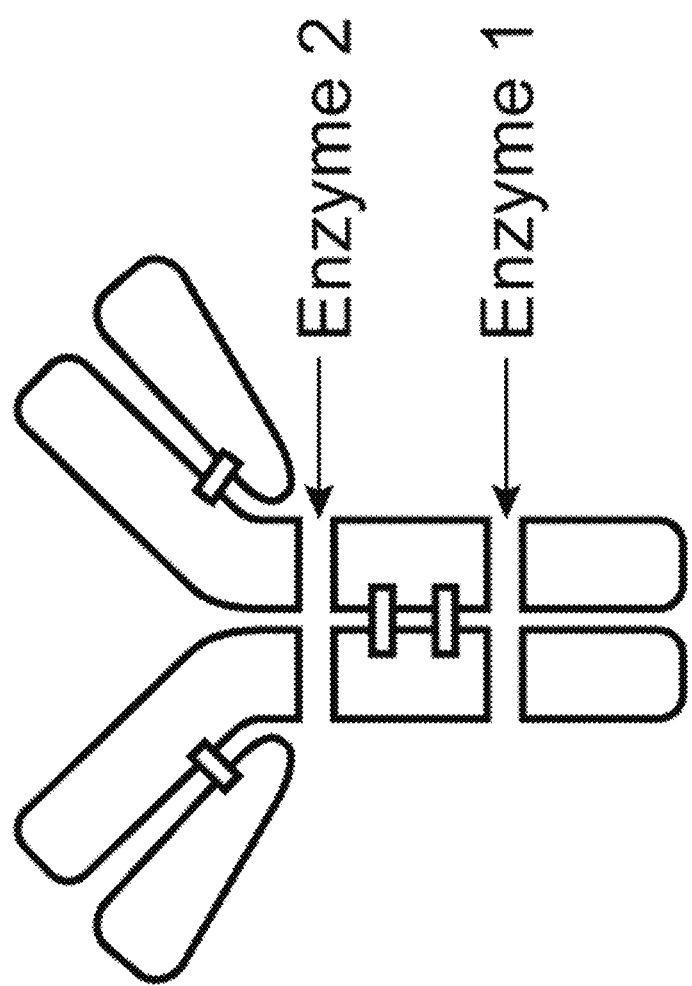
FIG. 20. A schematic representation of an antibody or conjugate treated with an enzyme that cuts below the hinge and a second enzyme that cuts above the hinge.

A benefit of the TNB conjugation process is the significant decrease or complete elimination of hinge disulfide reduction on the antibody, and thus production of a conjugate having the native interchain disulfide bonds. An assay was developed to measure the level of hinge scrambling in both the antibody and the conjugate. In the assay, the antibody or conjugate is treated with an enzyme that cuts below the hinge and a second enzyme that cuts above the hinge, as shown in FIG. 20.

The hinge fragment is then analyzed by HPLC or LC-MS to determine the amount of native and scrambled hinge that was present in the antibody or conjugate.

A 1 mg/mL ADC sample was treated with IdeS (Enzyme 1, 1 unit/µg ADC) at 37° C. for 30 minutes followed by treatment with Lys-C(Enzyme 2, 1 µg/150 µg ADC) at 37° C. for 5 minutes. The reaction was then quenched with trifluoroacetic acid. The sample was analyzed by HPLC: Waters XBridge BEH C18 column, column temperature: 60° C., mobile phase A: 0.1% TFA in water, mobile phase B: 0.1% TFA in acetonitrile, gradient: 20-30% mobile phase B over 30 minutes, flow rate: 0.2 mL/min, UV detection at 214 nm. Peaks were confirmed by MS.

Example 16: Comparison with Conjugation to Cysteine-Capped Antibody

ADC produced from cysteine-capped antibody contains hinge-scrambled product. To conjugate a cysteine-capped antibody, the antibody must be fully reduced with excess tris(2-carboxyethyl)phosphine hydrochloride (TCEP) and the reduced interchain disulfide bonds reoxidized with dehydroascorbic acid, leaving only the mutated cysteine residues available as free thiols for conjugation. The mutated cysteine residues are then conjugated to linker-payload to afford crude ADC. The reoxidation step produces both native interchain disulfide bonds and scrambled disulfide bonds at the hinge region of the antibody. For ADCs produced by this full reduction/reoxidation process, the level of hinge scrambling measured by the assay described in Example 15 is typically 5-20%. Note that all hinge scrambling originates from the ADC conjugation process, as hinge scrambling has not been detected in the starting antibody.

To 4.0 g (27.6 µmol; 27 mg/mL in 60 mM histidine, pH 7; 144 mL) of cysteine-capped trastuzumab K183C-K290C antibody was added 1.65 mL of 0.5M TCEP (30 equivalents; 0.827 mmol; 0.5M solution in water). The reaction mixture was incubated at 370C for 5 h, and then buffer exchanged by diafiltration (TangenX ProStream 50 kD membrane, 110-210 g/m$^2$, 10 diavolumes of 60 mM histidine, pH 7). Following diafiltration, the mixture was cooled to 4° C., 0.144 g dehydroascorbic acid (30 equivalents; 0.827 mmol; 50 mM in 1:1 DMSO/water; 16.5 mL) was added, and the mixture was incubated at 4° C. for approximately 16 h. The mixture was heated to 25° C., 0.185 g of mcvcPABC0101 linker-payload (5 quivalents, 0.138 mmol; 25 mM in dimethylsulfoxide; 5.51 mL) was added, and the mixture was incubated at 25° C. for 1 h to afford crude conjugate. Following HIC purification, the level of hinge scrambling in the ADC measured by the assay described in Example 15 was 18%.

For comparison, ADCs produced from TNB-capped antibody, as in Examples 6, 7, and 9 above, contain no detectable hinge scrambling after HIC purification as measured by the assay described in Example 15.

We claim:
1. A process for conjugating a 5-thio-2-nitrobenzoic acid (TNB)-capped cysteine-containing protein, the method comprising the steps of:
    (a) reacting the TNB-capped cysteine-containing protein with an about a 4:1 to 6:1 stoichiometric excess of tris (3-sulfophenyl) phosphine (TSPP) to capped cysteine residues, optionally in the presence of sodium chloride;
    (b) filtering the reaction mixture of step (a) to remove one or more of excess reducing agent and detached TNB;
    (c) adjusting the temperature of the filtered mixture of step (b) to between about 4 and about 25 degrees Celsius;
    (d) contacting the reaction mixture of step (c) with dehydroascorbic acid and agitating the resulting mixture for between about 0.5 and about 16 hours; and
    (e) adding linker-payload to the mixture of step (d) and agitating the resulting mixture at about 25 degrees Celsius.

2. The process of claim 1, wherein the stoichiometric excess is about 5:1 reducing agent to capped cysteine residues.

3. The process of claim 1, wherein step (c) and (d) are performed at about 25 degrees Celsius.

4. The process of claim 3, wherein in step (d) the reaction mixture of step (c) and the dehydroascorbic acid are agitated for about 0.5 hours.

5. The process of claim 1, wherein step (c) and (d) are performed at about 4 degrees Celsius.

6. The process of claim 5, wherein in step (d) the reaction mixture of step (c) and the dehydroascorbic acid are agitated for about 16 hours.

7. The process of claim 1, further comprising the steps of:
(f) adding excess cysteine after step (e) to quench the reaction of the said linking moiety; and
(g) separating the quenched linker-payload from the conjugate.

8. The process of claim 7, wherein the separation of step (g) is performed by diafiltration or column chromatography.

9. The process of claim 8, wherein the column chromatography is hydrophobic interaction chromatography (HIC).

10. The process of claim 9, wherein one or more isopropanol-containing buffers are used to perform the HIC purification.

11. The process of claim 1, wherein the cysteine-containing protein is an antibody.

12. The process of claim 1, wherein the cysteine-containing protein is an antibody selected from an anti-EDB antibody and an anti-HER2 antibody.

13. The process of claim 12, wherein the anti-HER2 antibody is trastuzumab.

* * * * *